(12) United States Patent
Lang et al.

(10) Patent No.: US 8,290,564 B2
(45) Date of Patent: *Oct. 16, 2012

(54) METHOD FOR BONE STRUCTURE PROGNOSIS AND SIMULATED BONE REMODELING

(75) Inventors: Philipp Lang, Lexington, MA (US);
Daniel Steines, Palo Alto, CA (US);
Claude Arnaud, Mill Valley, CA (US);
Siau-Way Liew, Pinole, CA (US); Rene Vargas-Voracek, Sunnyvale, CA (US)

(73) Assignee: ImaTx, Inc., Burlington, MA (US)

( * ) Notice: Subject to any disclaimer, the term of this patent is extended or adjusted under 35 U.S.C. 154(b) by 254 days.

This patent is subject to a terminal disclaimer.

(21) Appl. No.: 11/846,018

(22) Filed: Aug. 28, 2007

(65) Prior Publication Data

US 2008/0031412 A1    Feb. 7, 2008

Related U.S. Application Data

(63) Continuation-in-part of application No. 10/944,478, filed on Sep. 17, 2004, now Pat. No. 8,073,521.

(60) Provisional application No. 60/823,736, filed on Aug. 28, 2006, provisional application No. 60/503,916, filed on Sep. 19, 2003.

(51) Int. Cl.
*A61B 5/00* (2006.01)

(52) U.S. Cl. .................................................. 600/407

(58) Field of Classification Search ................. None
See application file for complete search history.

(56) References Cited

U.S. PATENT DOCUMENTS

| | | | |
|---|---|---|---|
| 2,274,808 A | 3/1942 | Rinn | 250/69 |
| 3,924,133 A | 12/1975 | Reiss | 250/408 |
| 4,012,638 A | 3/1977 | Altschuler et al. | 250/491 |
| 4,126,789 A | 11/1978 | Vogl et al. | 250/505 |
| 4,233,507 A | 11/1980 | Volz | 250/252 |
| 4,251,732 A | 2/1981 | Fried | 250/479 |
| 4,298,800 A | 11/1981 | Goldman | 250/445 T |
| 4,356,400 A | 10/1982 | Polizzi et al. | 378/138 |
| 4,400,827 A | 8/1983 | Spears | 378/207 |
| 4,593,400 A | 6/1986 | Mouyen | 378/99 |
| 4,649,561 A | 3/1987 | Arnold | 378/207 |
| 4,686,695 A | 8/1987 | Macovski | 378/146 |
| 4,721,112 A | 1/1988 | Hirano et al. | 128/659 |

(Continued)

FOREIGN PATENT DOCUMENTS

CA    2342344    3/2000

(Continued)

OTHER PUBLICATIONS

Blake et al., "Active Contours; The Application of Techniques from Graphics, Vision, Control Theory and Statistics to Visual Tracking of Shapes in Motion," *Springer Verlag*, Title Page and Table of Contents pages only (ISBN 3540762175) (1999).

(Continued)

*Primary Examiner* — Jacqueline Cheng
(74) *Attorney, Agent, or Firm* — Sunstein Kann Murphy & Timbers LLP

(57) ABSTRACT

Described herein are methods for analyzing bone structure and/or bone density, methods for estimating fracture risk in a subject as well as methods for monitoring the efficacy of an agent on bone structure and/or bone density.

18 Claims, 11 Drawing Sheets

U.S. PATENT DOCUMENTS

| | | | | |
|---|---|---|---|---|
| 4,782,502 A | 11/1988 | Schulz | | 378/18 |
| 4,922,915 A | 5/1990 | Arnold et al. | | 128/653 R |
| 4,956,859 A | 9/1990 | Lanza et al. | | 378/157 |
| 4,985,906 A | 1/1991 | Arnold | | 378/18 |
| 5,001,738 A | 3/1991 | Brooks | | 378/170 |
| 5,090,040 A | 2/1992 | Lanza et al. | | 378/62 |
| 5,122,664 A | 6/1992 | Ito et al. | | 250/327.2 |
| 5,127,032 A | 6/1992 | Lam et al. | | 378/189 |
| 5,150,394 A | 9/1992 | Karellas | | 378/62 |
| 5,172,695 A | 12/1992 | Cann et al. | | 128/653.1 |
| 5,187,731 A | 2/1993 | Shimura | | 378/207 |
| 5,200,993 A | 4/1993 | Wheeler et al. | | 379/96 |
| 5,222,021 A | 6/1993 | Feldman et al. | | 364/413.14 |
| 5,228,445 A | 7/1993 | Pak et al. | | 128/660.01 |
| 5,235,628 A | 8/1993 | Kalender | | 378/207 |
| 5,247,934 A | 9/1993 | Wehrli et al. | | 600/410 |
| 5,270,651 A | 12/1993 | Wehrli | | 324/308 |
| 5,271,401 A | 12/1993 | Fishman | | 128/654 |
| 5,320,102 A | 6/1994 | Paul et al. | | 128/653.2 |
| 5,335,260 A | 8/1994 | Arnold | | 378/207 |
| 5,384,643 A | 1/1995 | Inga et al. | | 358/403 |
| 5,476,865 A | 12/1995 | Panetta et al. | | 514/369 |
| 5,493,593 A | 2/1996 | Müller et al. | | 378/19 |
| 5,493,601 A | 2/1996 | Fivez et al. | | 378/207 |
| 5,513,240 A | 4/1996 | Hausmann et al. | | 378/170 |
| 5,521,955 A | 5/1996 | Gohno et al. | | 378/18 |
| 5,537,483 A | 7/1996 | Stapleton et al. | | 382/309 |
| 5,562,448 A | 10/1996 | Mushabac | | 433/215 |
| 5,565,678 A | 10/1996 | Manian | | 250/252.1 |
| 5,592,943 A | 1/1997 | Buhler et al. | | 128/661.03 |
| 5,600,574 A | 2/1997 | Reitan | | 364/552 |
| 5,657,369 A | 8/1997 | Stein et al. | | 378/208 |
| 5,673,298 A * | 9/1997 | Mazess | | 378/54 |
| 5,687,210 A | 11/1997 | Maitrejean et al. | | 378/57 |
| 5,769,072 A | 6/1998 | Olsson et al. | | 128/205.13 |
| 5,769,074 A | 6/1998 | Barnhill et al. | | 128/630 |
| 5,772,592 A | 6/1998 | Cheng et al. | | 600/407 |
| 5,852,647 A | 12/1998 | Schick et al. | | 378/53 |
| 5,864,146 A | 1/1999 | Karellas | | 250/581 |
| 5,886,353 A | 3/1999 | Spivey et al. | | 250/370.09 |
| 5,915,036 A | 6/1999 | Grunkin et al. | | 382/132 |
| 5,917,877 A | 6/1999 | Chiabrera et al. | | 378/5.3 |
| 5,931,780 A | 8/1999 | Giger et al. | | 600/407 |
| 5,945,412 A | 8/1999 | Fuh et al. | | 514/176 |
| 5,948,692 A | 9/1999 | Miyauti et al. | | 436/501 |
| 6,029,078 A | 2/2000 | Weinstein et al. | | 600/407 |
| 6,064,716 A | 5/2000 | Siffert et al. | | 378/53 |
| 6,077,224 A | 6/2000 | Lang et al. | | 600/437 |
| 6,108,635 A | 8/2000 | Herren et al. | | 514/573 |
| 6,156,799 A | 12/2000 | Hartke et al. | | 514/573 |
| 6,178,225 B1 | 1/2001 | Zur et al. | | 378/98.2 |
| 6,205,348 B1 | 3/2001 | Giger et al. | | 600/407 |
| 6,215,846 B1 | 4/2001 | Mazess et al. | | 378/62 |
| 6,226,393 B1 | 5/2001 | Grunkin et al. | | 382/128 |
| 6,246,745 B1 | 6/2001 | Bi et al. | | 378/54 |
| 6,248,063 B1 | 6/2001 | Barnhill et al. | | 600/300 |
| 6,249,692 B1 | 6/2001 | Cowin | | 600/407 |
| 6,252,928 B1 | 6/2001 | MacKenzie | | 378/54 |
| 6,285,901 B1 | 9/2001 | Taicher et al. | | 600/410 |
| 6,289,115 B1 | 9/2001 | Takeo | | 382/130 |
| 6,302,582 B1 | 10/2001 | Nord et al. | | 378/207 |
| 6,306,822 B1 | 10/2001 | Kumagai et al. | | 514/7 |
| 6,315,553 B1 | 11/2001 | Sachdeva et al. | | 433/24 |
| 6,320,931 B1 | 11/2001 | Arnold | | 378/56 |
| 6,377,653 B1 | 4/2002 | Lee et al. | | 378/54 |
| 6,411,729 B1 | 6/2002 | Grunkin | | 382/132 |
| 6,430,427 B1 | 8/2002 | Lee et al. | | 600/407 |
| 6,442,287 B1 | 8/2002 | Jiang et al. | | 382/132 |
| 6,449,502 B1 | 9/2002 | Ohkubo | | 600/407 |
| 6,463,344 B1 | 10/2002 | Pavloskaia et al. | | 700/98 |
| 6,501,827 B1 | 12/2002 | Takasawa | | 378/116 |
| 6,556,698 B1 | 4/2003 | Diano et al. | | 382/132 |
| 6,690,761 B2 | 2/2004 | Lang et al. | | 378/56 |
| 6,694,047 B1 | 2/2004 | Farrokhnia et al. | | 382/132 |
| 6,717,174 B2 | 4/2004 | Karellas | | 250/582 |
| 6,775,401 B2 * | 8/2004 | Hwang et al. | | 382/131 |
| 6,799,066 B2 | 9/2004 | Steines et al. | | 600/407 |
| 6,807,249 B2 | 10/2004 | Dinten et al. | | 378/54 |
| 6,811,310 B2 | 11/2004 | Lang et al. | | 378/169 |
| 6,824,309 B2 | 11/2004 | Robert-Coutant et al. | | 378/207 |
| 6,829,378 B2 | 12/2004 | DiFilippo et al. | | 382/128 |
| 6,835,377 B2 | 12/2004 | Goldberg et al. | | 424/93.7 |
| 6,836,557 B2 | 12/2004 | Tamez-Pena et al. | | 382/128 |
| 6,895,077 B2 | 5/2005 | Karellas et al. | | 378/98.3 |
| 6,904,123 B2 | 6/2005 | Lang | | 378/54 |
| 6,934,590 B2 | 8/2005 | Ogawa | | 700/19 |
| 6,975,894 B2 | 12/2005 | Wehrli et al. | | 600/407 |
| 7,050,534 B2 | 5/2006 | Lang | | 378/54 |
| 7,058,159 B2 | 6/2006 | Lang et al. | | 378/54 |
| 7,120,225 B2 | 10/2006 | Lang et al. | | 378/54 |
| 7,184,814 B2 | 2/2007 | Lang et al. | | 600/416 |
| 7,239,908 B1 | 7/2007 | Alexander et al. | | 600/427 |
| 7,245,697 B2 | 7/2007 | Lang | | 378/54 |
| 7,283,857 B1 | 10/2007 | Fallon et al. | | 600/407 |
| 7,292,674 B2 | 11/2007 | Lang | | 378/54 |
| 7,379,529 B2 | 5/2008 | Lang | | 378/54 |
| 7,467,892 B2 | 12/2008 | Lang et al. | | 378/207 |
| 7,545,964 B2 | 6/2009 | Lang et al. | | 382/128 |
| 7,580,504 B2 | 8/2009 | Lang et al. | | 378/56 |
| 7,660,453 B2 | 2/2010 | Lang | | 382/132 |
| 7,664,298 B2 | 2/2010 | Lang et al. | | 382/128 |
| 7,676,023 B2 | 3/2010 | Lang | | 378/54 |
| 7,840,247 B2 | 11/2010 | Liew et al. | | 600/407 |
| 2002/0087274 A1 | 7/2002 | Alexander et al. | | 702/19 |
| 2002/0159567 A1 | 10/2002 | Sako et al. | | 378/117 |
| 2002/0186818 A1 | 12/2002 | Arnaud et al. | | 378/165 |
| 2002/0191823 A1 | 12/2002 | Wehrli et al. | | 382/128 |
| 2002/0194019 A1 | 12/2002 | Evertsz | | 705/2 |
| 2002/0196966 A1 | 12/2002 | Jiang et al. | | 382/132 |
| 2003/0015208 A1 | 1/2003 | Lang et al. | | 128/922 |
| 2003/0112921 A1* | 6/2003 | Lang et al. | | 378/54 |
| 2003/0198316 A1 | 10/2003 | Dewaele et al. | | 378/54 |
| 2004/0106868 A1 | 6/2004 | Liew et al. | | 600/442 |
| 2004/0242987 A1 | 12/2004 | Liew et al. | | 600/407 |
| 2004/0247074 A1 | 12/2004 | Langton | | 378/54 |
| 2005/0015002 A1 | 1/2005 | Dixon et al. | | 600/407 |
| 2005/0148860 A1 | 7/2005 | Liew et al. | | 600/410 |
| 2005/0240096 A1 | 10/2005 | Ackerman et al. | | 600/410 |
| 2006/0062442 A1 | 3/2006 | Arnaud et al. | | 382/128 |
| 2007/0047794 A1 | 3/2007 | Lang et al. | | 382/132 |
| 2007/0274442 A1 | 11/2007 | Gregory et al. | | 378/54 |
| 2008/0031412 A1 | 2/2008 | Lang et al. | | 378/54 |
| 2008/0058613 A1 | 3/2008 | Lang et al. | | 600/300 |
| 2008/0097794 A1 | 4/2008 | Arnaud et al. | | 705/3 |
| 2008/0219412 A1 | 9/2008 | Lang | | 378/207 |
| 2009/0207970 A1 | 8/2009 | Lang | | 378/38 |
| 2009/0225958 A1 | 9/2009 | Lang | | 378/207 |
| 2010/0014636 A1 | 1/2010 | Lang et al. | | 378/56 |
| 2010/0098212 A1 | 4/2010 | Lang | | 378/54 |
| 2010/0130832 A1 | 5/2010 | Lang et al. | | 600/300 |
| 2010/0197639 A1 | 8/2010 | Lang et al. | | 514/143 |
| 2010/0210972 A1 | 8/2010 | Vargas-Voracek | | 600/587 |
| 2011/0036360 A1 | 2/2011 | Lang et al. | | 128/898 |
| 2011/0040168 A1 | 2/2011 | Arnaud et al. | | 600/407 |
| 2011/0105885 A1 | 5/2011 | Liew et al. | | 600/410 |

FOREIGN PATENT DOCUMENTS

| | | |
|---|---|---|
| DE | 19853965 | 5/2000 |
| EP | 0314506 | 5/1989 |
| EP | 0797952 | 10/1997 |
| EP | 0570936 | 8/2000 |
| EP | 0678191 | 2/2001 |
| EP | 1230896 | 8/2002 |
| EP | 1283492 | 2/2003 |
| EP | 1349098 | 10/2003 |
| EP | 1357480 | 10/2003 |
| EP | 1424650 | 6/2004 |
| EP | 1598778 | 11/2005 |
| EP | 1069395 | 7/2006 |
| GB | 2023920 | 1/1980 |
| JP | 62 266053 | 11/1987 |
| JP | 05 099829 | 4/1993 |
| JP | 08 186762 | 7/1996 |
| JP | 10 145396 | 5/1998 |
| JP | 10 262959 | 10/1998 |
| JP | 11 069136 | 3/1999 |
| JP | 11 112877 | 4/1999 |

| | | |
|---|---|---|
| JP | 2002 045722 | 2/2000 |
| JP | 2000 126168 | 5/2000 |
| JP | 2000 139889 | 5/2000 |
| JP | 2003 230557 | 8/2003 |
| WO | WO 94/012855 | 6/1994 |
| WO | WO 95/014431 | 6/1995 |
| WO | WO 99/08597 | 2/1999 |
| WO | WO 99/45371 | 9/1999 |
| WO | WO 99/45845 | 9/1999 |
| WO | WO 99/52331 | 10/1999 |
| WO | WO 00/33157 | 6/2000 |
| WO | WO 00/72216 | 11/2000 |
| WO | WO 01/38824 | 5/2001 |
| WO | WO 01/63488 | 8/2001 |
| WO | WO 01/65449 | 9/2001 |
| WO | WO 02/17789 | 3/2002 |
| WO | WO 02/22014 | 3/2002 |
| WO | WO 02/30283 | 4/2002 |
| WO | WO 02/096284 | 12/2002 |
| WO | WO 03/071934 | 9/2003 |
| WO | WO 03/073232 | 9/2003 |
| WO | WO 03/088085 | 10/2003 |
| WO | WO 2004/019256 | 3/2004 |
| WO | WO 2004/025541 | 3/2004 |
| WO | WO 2004/062495 | 7/2004 |
| WO | WO 2004/086972 | 10/2004 |
| WO | WO 2004/096048 | 11/2004 |
| WO | WO 2005/027732 | 3/2005 |
| WO | WO 2006/033712 | 3/2006 |
| WO | WO 2006/034018 | 3/2006 |
| WO | WO 2008/034101 | 3/2008 |

OTHER PUBLICATIONS

Bushberg et al., "Essential Physics of Medical Imaging," *Lipincott, Williams & Wilkins*, Title Page and Table of Contents pages only (ISBN 0683011405) (2002).
Cann, "Quantitative CT for Determination of Bone Mineral Density: A Review," *Radiology* 166:509-522 (1988).
Castleman, K., Digital Image Processing, *Prentice Hall* Title page and Table of Contents pages only (ISBN 0132114674) (1996).
Cummings, SR et al., "Bone Density at Various Sites for Prediction of Hip Fractures," *Lancet* 341:72-75 (1993).
Eastell et al., "Treatment of postmenopausal Osteoporosis," *New Engl. J. of Med.* 338:736-746 (1988).
Faulker, KG, "Bone Densitometry: Choosing the Right Skeletal Site to Measure," *J. Clin. Densitometry*, 1:279-85 (1998).
Gluer et al., "Peripheral Measurement Techniques for the Assessment of Osteoporosis," *Semin Nucl. Med.* 27:229-247 (1997).
Gluer et al., "Quantitative Ultrasound Techniques for the Assessment of Osteoporosis—Expert Agreement on Current Status," *J Bone Miner Res.* 12:1280-1288 (1997).
Hosking, D. et al., "Prevention of Bone Loss in Postmenopausal Women Under 60 Years of Age. Early Postmenopausal Intervention Cohort Study Group," *N Engl J. Med.* 338:485-492 (1998).
Lam et al., "X-Ray Diagnosis: A Physician's Approach", Editor Lam, 1998, Springer-Verlag publishers, Title page and Table of Contents pgs. Only (ISBN 9813083247).
Marshall, D. et al., "Meta-Analysis of How Well Measures of Bone Mineral Density Predict Occurrence of Osteoporotic Fractures," *Br Med J.* 312:1254-1259 (1996).
Njef, CF et al., "The Role of Ultrasound in the Assessment of Osteoporosis: A Review," *Osteoporosis Int* 7:7-22 (1997).
Njef, CF et al., "Quantitative Ultrasound: Assessment of Osteoporosis and Bone Status," London, England: *Martin Dunitz*, Title page and Table of Contents pages only (ISBN 1853176796) (1999).
Patel et al., "Radiation Dose to the Patient and Operator from a Peripheral Dual X-Ray Absorptiometry System," *Journal of Clinical Densitometry* 2(4):397-401 (1999).
Ruttiman, UE et al. "Fractal Dimension from Radiographs of Peridontal Alveolar Bone. A Possible Diagnostic Indicator of Osteoporosis," *Oral Surg Oral Med Oral Pathol* 74:98-110 (1992).
Shrout et al., "Comparison of Morphological Measurements Extracted from Digitized Dental Radiographs with Lumbar and Femoral Bone Mineral Density Measurements in Post," *J. Periondontal* 71:335-340 (2000).
Slone et al., "Body CT: A Practical Approach", Editor Slone, 1999 McGraw-Hill publishers, Title page and Table of Contents pgs. Only (ISBN 007058219).
Southard KA and Southard TE, "Quantitative Features of Digitized Radiographic Bone Profiles," *Oral Surgery, Oral Medicine, and Oral Pathology* 73(6):751-9 (1992).
Stout et al., "X-Ray Structure Determination: A Practical Guide", $2^{nd}$ Ed. Editors Stout and Jensen, 1989, John Wiley & Sons, Title pagend Table of Contents pgs. Only (ISBN 0471607118).
Svendsen OL et al., "Impact of Soft Tissue on In-Vivo Accuracy of Bone Mineral Measurements in the Spine, Hip, and Forearm: A Human Cadaver Study," *J Bone Miner Res.* 10:868-873 (1995).
Tothill, P. et al., "Errors due to Non-Uniform Distribution of Fat in Dual X-Ray Absorptiometry of the Lumbar Spine," *Br J Radiol.* 65:807-813 (1992).
Verhoeven et al. "Densitometric Measurement of the Mandible: Accuracy and Validity of Intraoral Versus Extraoral Radiographic Techniques in an In Vitro STudy,"*Clin Oral Impl Res*, 9:333-342 (1998).
White, SC and Rudolph, DJ, "Alternations of the Trabecular Pattern in the Jaws of Patients with Osteoporosis," *Oral Surg. Oral Med. Oral Pathol. Oral Radiol. and Endod*. 88:628-635 (1999).
International Searching Authority, International Search Report—International Application No. PCT/US04/30718, dated Jan. 4, 2007.
European Patent Office, Supplementary Partial European Search Report—Application No. EP 04 78 8838, dated Oct. 22, 2007, 3 pages.
Barker, "Case Method: Entity Relationship Modeling" (Computer Aided Systems Engineering), $1^{st}$ Ed., Addison-Wesley Longman Pub. Co., Inc., publisher, 2 pages (Abstract Pages Only) (1990).
Bauer et al., "Biochemical Markers of Bone Turnover and Prediction of Hip Bone Loss in Older Women: The Study of Osteoporotic Fractures," *Journal of Bone and Mineral Research*, vol. 14, pp. 1404-1410 (1999).
Beck et al., "Experimental Testing of a DEXA-Derived Curved Beam Model of the Proximal Femur," *Journal of Orthopaedic Research*, vol. 16, No. 3, pp. 394-398 (1998).
Black et al., "An Assessment Tool for Predicting Fracture Risk in Postmenopausal Women" *Osteoporosis International*, vol. 12, pp. 519-528 (2001).
Cheal et al., "Role of Loads & Prosthesis Material Properties on the Mechanics of the Proximal Femur After Total Hip Arthroplasty," *J. Orthop. Res*., vol. 10, No. 3, pp. 405-422 (1992).
Cootes et al., "Anatomical statistical models and their role in feature extraction," *The British Journal of Radiology*, Special Issue, 7 pages [S133-S139] (2004).
Cootes et al., "Statistical models of appearance for medical image analysis and computer vision," *Proc. SPIE Medical Imaging*, 14 pages, (2001).
Cootes, "An Introduction to Active Shape Models," *Image Processing and Analysis*, Ch. 7, pp. 1-26 (2000).
Cortet et al., "Bone Microarchitecture and Mechanical Resistance," *Joint Bone Spine*, vol. 68, pp. 297-305 (2001).
Crabtree et al., "Improving Risk Assessment: Hip Geometry, Bone Mineral Distribution and Bone Strength in Hip Fracture Cases and Controls. The EPOS Study," *Osteoporos Int*., vol. 13, pp. 48-54 (2002).
Crawley, "In Vivo Tissue Characterization Using Quantitative Computed Tomography: A Review," *Journal of Medical Engineering & Technology*, vol. 14, No. 6, pp. 233-242 (1990).
Davies et al., "A Minimum Description Length Approach to Statistical Shape Modeling," IEEE Transaction on Medical Imaging, vol. 21, No. 5, pp. 525-537 (2002).
Duryea et al., "New radiographic-based surrogate outcome measures for osteoarthritis of the knee," *Osteoarthritis and Cartilage*, vol. 11, pp. 102-110 (2003).
Duryea et al., "Trainable rule-based algorithm for the measurement of joint space width in digital radiographic images of the knee," *Medical Physics*, vol. 27, No. 3, pp. 580-591 (2000).
Engelman et al., "Impact of Geographic Barriers on the Utilization of Mammograms by Older Rural Women, "*Journal of the American Geriatrics Society*, vol. 50, No. 1, pp. 62-68 (2002).

Fleute et al., "Statistical model registration for a C-arm CT system," Computer Science Department, The Johns Hopkins University, pp. 1667-1670 (2002).

Fleute et al., "Nonrigid 3-D/2-D Registration of Images Using Statistical Models," pp. 138-147 (1999).

Gilliland et al., "Patterns of Mammography Use Among Hispanic, American Indian, and Non-Hispanic White Women in New Mexico, 1994-1997," *American Journal of Epidemiology*, vol. 152, No. 5, pp. 432-437 (2000).

Grisso et al., "Risk Factors for Falls as a Cause of Hip Fracture in Women. The Northeast Hip Fracture Study Group," *N. Engl. J. Med.*, (Abstract Page Only), 1 page, vol. 324, No. 19, pp. 1326-1331 (1991).

Gudmundsdottir et al., "Vertebral Bone Density in Icelandic Women Using Quantitative Computed Tomography Without an External Reference Phantom," *Osteoporosis Int.*, vol. 3, pp. 84-89 (1993).

Hayes et al., "Biomechanics of Cortical and Trabecular Bone: Implications for Assessment of Fracture Risk," Basic Orthopaedic Biomechanics, 2nd Ed., Ch. 3, pp. 69-111, Lippincott-Raven, publishers (1997).

Hayes et al., "Biomechanics of Fracture Risk Prediction of the Hip and Spine by Quantitative Computed Tomography," *Radiologic Clinics of North America*, vol. 29, No. 1, pp. 1-18 (1991).

Hayes et al. "Impact Near the Hip Dominates Fracture Risk in Elderly Nursing Home Residents Who Fall," *Calcif. Tissue Int.* (Abstract Page Only), 1 page, vol. 52, No. 3 (1993).

Hedström et al., "Biochemical Bone Markers and Bone Density in Hip Fracture Patients," *Acta Orthop. Scand.*, vol. 71, No. 4, pp. 409-413 (2000).

Horn, "Closed-form solution of absolute orientation using unit quaternions," *J. Opt. Soc. of Am. A*, vol. 4, No. 4, pp. 629-642 (1987).

Ikuta et al., "Quantitative Analysis Using the Star Volume Method Applied to Skeleton Patterns Extracted with a Morphological Filter," *Journal of Bone and Mineral Metabolism*, vol. 18, pp. 271-277 (2000).

Jacobs et al., "Long-term Bone Mass Evaluation of Mandible and Lumbar Spine in a Group of Women Receiving Hormone Replacement Therapy," *European Journal Oral Science*, vol. 104, pp. 10-16 (1996).

Jazieh et al., "Mammography Utilization Pattern Throughout the State of Arkansas: A Challenge for the Future," *Journal of Community Health*, vol. 26, No. 4, pp. 249-255 (2001).

Jeffcoat et al., "Post-menopausal bone loss and its relationship to oral bone loss", *Periodontology*, vol. 23, pp. 94-102 (2000).

Klose "Teleradiology—A Model for Remote Consultation," *Electromedica*, vol. 66, No. 1, pp. 37-41 (1998).

Kumasaka et al., "Initial Investigation of Mathematical Morphology for the Digital Extraction of the Skeletal Characteristics of Trabecular Bone," Departments of Oral Surgery and Oral and Maxillofacial Radiology, Kanagawa Dental College, Japan, pp. 161-168 (1996).

Lang et al., "Osteoporosis—Current Techniques and Recent Developments in Quantitative Bone Densitometry" *Radiologic Clinics of North America*, vol. 29, No. 1, pp. 49-76 (1991).

Metrabio Website, "QUS-2 Calcaneal Ultrasonometer," What's New: Ultrasound, Retrieved from the interne—http://www.metrabio.com/html/_prods/L3-ultrasound-r.ht, 2 pages (2001).

Mourtada et al., "Curved Beam Model of the Proximal Femur for Estimating Stress Using Dual-Energy X-Ray Absorptiometry Derived Structural Geometry," *J. Ortho. Res.*, vol. 14, No. 3, pp. 483-492 (1996).

Ouyang et al., "Morphometric Texture Analysis of Spinal Trabecular Bone Structure Assessed Using Orthogonal Radiographic Projections," *Med. Phys.*, vol. 25, No. 10, pp. 2037-2045 (1998).

Pharoah, "X-Ray Film, Intensifying Screens, and Grids," Ch. 4, Section 4: Imaging Principles and Techniques, *Oral Radiology*, 4th ed., pp. 68-76 (2000).

Pinilla et al., "Impact Direction from a Fall Influences the Failure Load of the Proximal Femur as Much as Age-Related Bone Loss," *Calcified Tissue International*, vol. 58, pp. 231-235 (1996).

Riggs et al., "Changes in Bone Mineral Density of the Proximal Femur and Spine with Aging: Differences Between the Postmenopausal and Senile Osteoporosis Syndromes," *J. Clin. Invest.*, vol. 70, pp. 716-723 (1982).

Russ, "The Image Processing Handbook," 3rd Edition, North Carolina State Univ., Chapter 7: Processing Binary Images, pp. 494-501, CRC/IEEE Press, publisher (1998).

Sandler et al., "An Analysis of the Effect of Lower Extremity Strength on Impact Severity During a Backward Fall," *Journal of Biomechanical Engineering*, Transactions of the ASME, vol. 123, pp. 590-598 (2001).

Southard et al., "The Relationship Between the Density of the Alveolar Processes and that of Post-cranial Bone," *J. Dent. Res.*, vol. 79, No. 4, pp. 964-969 (2000).

van den Kroonenberg et al., "Dynamic Models for Sideways Falls from Standing Height," *Journal of Biomechanical Engineering*, vol. 117, pp. 309-318 (1995).

Yoshikawa et al., "Geometric Structure of the Femoral Neck Measured Using Dual-Energy X-Ray Absorptiometry," *J. Bone Miner. Res.*, vol. 10, No. 3, p. 510 (Abstract Only) (1995).

International Searching Authority, Written Opinion of International Searching Authority—Appl. No. PCT/US2004/030718, dated Jan. 4, 2007 (3 pages).

Fleute et al., "Incorporating a statistically based shape model into a system for computer-assisted anterior cruciate ligament surgery," Medical Image Analysis, vol. 3, No. 3, pp. 209-222 (1999).

United States Patent and Trademark Office, Final Office Action—U.S. Appl. No. 10/944,478, dated Nov. 26, 2010 (8 pages).

Geraets et al., "A New Method for Automatic Recognition of the Radiographic Trabecular Pattern," J. Bone and Mm. Res., Department of Oral Radiology, vol. 5, No. 3, pp. 227-233 (1990).

International Searching Authority, International Preliminary Report on Patentability—Appl. No. PCT/US2004/030718 dated Mar. 6, 2007 (4 pages).

United States Patent and Trademark Office, Non-Final Office Action—U.S. Appl. No. 10/944,478 dated Apr. 11, 2007 (9 pages).

Bromberg & Sunstein LLP Boston, MA, Response to Non-Final Office Action—U.S. Appl. No. 10/944,478, filed Oct. 10, 2007 (10 pages).

United States Patent and Trademark Office, Final Office Action—U.S. Appl. No. 10/944,478 dated Dec. 13, 2007 (8 pages).

Bromberg & Sunstein LLP Boston, MA, Amendment Accompanying Request for Continued Examination (RCE) to Final Office Action—U.S. Appl. No. 10/944,478 as filed Jun. 13, 2008 (13 pages).

United States Patent and Trademark Office, Non-Final Office Action—U.S. Appl. No. 10/944,478 dated Oct. 1, 2008 (8 pages).

Bromberg & Sunstein LLP Boston, MA, Response to Non-Final Office Action—U.S. Appl. No. 10/944,478 as filed Apr. 1, 2009 (12 pages).

United States Patent and Trademark Office, Final Office Action—U.S. Appl. No. 10/944,478 dated Jul. 21, 2009 (8 pages).

Sunstein Kann Murphy & Timbers LLP Boston, MA, Response Accompanied with Request for Continued Examination (RCE)—U.S. Appl. No. 10/944,478 as filed Jan. 21, 2010 (11 pages).

United States Patent and Trademark Office, Non-Final Office Action—U.S. Appl. No. 10/944,478 dated Mar. 1, 2010 (23 pages).

Sunstein Kann Murphy & Timbers LLP Boston, MA, Response to Non-Final Office Action—U.S. Appl. No. 10/944,478 as filed Sep. 1, 2010 (9 pages).

* cited by examiner

METHOD FOR BONE STRUCTURE PROGNOSIS AND SIMULATED BONE REMODELING

CROSS-REFERENCE TO RELATED APPLICATIONS

This application claims the benefit of U.S. provisional application Ser. No. 60/823,736, filed Aug. 28, 2006. This application is also a continuation-in-part of U.S. application Ser. No. 10/944,478, filed Sep. 17, 2004, which in turn claims the benefit of U.S. provisional application Ser. No. 60/503,916, filed Sep. 19, 2003. Each of the above-described documents is incorporated by reference herein in its entirety.

TECHNICAL FIELD

The present invention is in the field of imaging and analysis thereof. In particular, methods for accurately analyzing images to determine bone mineral density and/or bone structure are described along with methods for bone modeling and remodeling.

BACKGROUND

Imaging techniques are important diagnostic tools, particularly for bone related conditions. Currently available techniques for the noninvasive assessment of the skeleton for the diagnosis of osteoporosis or the evaluation of an increased risk of fracture include dual x-ray absorptiometry (DXA) (Eastell et al. (1998) *New Engl J. Med* 338:736-746); quantitative computed tomography (QCT) (Cann (1988) *Radiology* 166:509-522); peripheral DXA (pDXA) (Patel et al. (1999) *J Clin Densitom* 2:397-401); peripheral QCT (pQCT) (Gluer et. al. (1997) *Semin Nucl Med* 27:229-247); x-ray image absorptiometry (RA) (Gluer et. al. (1997) *Semin Nucl Med* 27:229-247); and quantitative ultrasound (QUS) (Njeh et al. "Quantitative Ultrasound: Assessment of Osteoporosis and Bone Status" 1999, Martin-Dunitz, London England; U.S. Pat. No. 6,077,224, incorporated herein by reference in its entirety). (See, also, WO 99/45845; WO 99/08597; and U.S. Pat. No. 6,246,745).

DXA of the spine and hip has established itself as the most widely used method of measuring BMD. Tothill, P. and D. W. Pye, (1992) *Br J Radiol* 65:807-813. The fundamental principle behind DXA is the measurement of the transmission through the body of x-rays of 2 different photon energy levels. Because of the dependence of the attenuation coefficient on the atomic number and photon energy, measurement of the transmission factors at 2 energy levels enables the area densities (i.e., the mass per unit projected area) of 2 different types of tissue to be inferred. In DXA scans, these are taken to be bone mineral (hydroxyapatite) and soft tissue, respectively. However, it is widely recognized that the accuracy of DXA scans is limited by the variable composition of soft tissue. Because of its higher hydrogen content, the attenuation coefficient of fat is different from that of lean tissue. Differences in the soft tissue composition in the path of the x-ray beam through bone compared with the adjacent soft tissue reference area cause errors in the BMD measurements, according to the results of several studies. Tothill, P. and D. W. Pye, (1992) *Br J Radiol*, 65:807-813; Svendsen, O. L., et al., (1995) *J Bone Min Res* 10:868-873. Moreover, DXA systems are large and expensive, ranging in price between $75,000 and $150,000.

Quantitative computed tomography (QCT) is usually applied to measure the trabecular bone in the vertebral bodies. Cann (1988) *Radiology* 166:509-522. QCT studies are generally performed using a single kV setting (single-energy QCT), when the principal source of error is the variable composition of the bone marrow. However, a dual-kV scan (dual-energy QCT) is also possible. This reduces the accuracy errors but at the price of poorer precision and higher radiation dose. Like DXA, however, QCT are very expensive and the use of such equipment is currently limited to few research centers.

Quantitative ultrasound (QUS) is a technique for measuring the peripheral skeleton. Njeh et al. (1997) *Osteoporosis Int* 7:7-22; Njeh et al. Quantitative Ultrasound: Assessment of Osteoporosis and Bone Status. 1999, London, England: Martin Dunitz. There is a wide variety of equipment available, with most devices using the heel as the measurement site. A sonographic pulse passing through bone is strongly attenuated as the signal is scattered and absorbed by trabeculae. Attenuation increases linearly with frequency, and the slope of the relationship is referred to as broadband ultrasonic attenuation (BUA; units: dB/MHz). BUA is reduced in patients with osteoporosis because there are fewer trabeculae in the calcaneus to attenuate the signal. In addition to BUA, most QUS systems also measure the speed of sound (SOS) in the heel by dividing the distance between the sonographic transducers by the propagation time (units: m/s). SOS values are reduced in patients with osteoporosis because with the loss of mineralized bone, the elastic modulus of the bone is decreased. There remain, however, several limitations to QUS measurements. The success of QUS in predicting fracture risk in younger patients remains uncertain. Another difficulty with QUS measurements is that they are not readily encompassed within the WHO definitions of osteoporosis and osteopenia. Moreover, no intervention thresholds have been developed. Thus, measurements cannot be used for therapeutic decision-making.

There are also several technical limitations to QUS. Many devices use a foot support that positions the patient's heel between fixed transducers. Thus, the measurement site is not readily adapted to different sizes and shapes of the calcaneus, and the exact anatomic site of the measurement varies from patient to patient. It is generally agreed that the relatively poor precision of QUS measurements makes most devices unsuitable for monitoring patients' response to treatment. Gluer (1997) *J Bone Min Res* 12:1280-1288.

Radiographic absorptiometry (RA) is a technique that was developed many years ago for assessing bone density in the hand, but the technique has recently attracted renewed interest. Gluer et al. (1997) *Semin Nucl Med* 27:229-247. With this technique, BMD is measured in the phalanges. The principal disadvantage of RA of the hand is the relative lack of high turnover trabecular bone. For this reason, RA of the hand has limited sensitivity in detecting osteoporosis and is not very useful for monitoring therapy-induced changes.

Peripheral x-ray absorptiometry methods such as those described above are substantially cheaper than DXA and QCT with system prices ranging between $15,000 and $35,000. However, epidemiologic studies have shown that the discriminatory ability of peripheral BMD measurements to predict spine and hip fractures is lower than when spine and hip BMD measurements are used. Cummings et al. (1993) *Lancet* 341:72-75; Marshall et al. (1996) *Br Med J* 312:1254-1259. The main reason for this is the lack of trabecular bone at the measurement sites used with these techniques. In addition, changes in forearm or hand BMD in response to hormone replacement therapy, bisphosphonates, and selective estrogen receptor modulators are relatively small, making such measurements less suitable than measurements of principally trabecular bone for monitoring response to treatment. Faulkner (1998) *J Clin Densitom* 1:279-285; Hoskings et al. (1998) *N Engl J Med* 338:485-492. Although attempts to obtain information on bone mineral density from dental x-rays have been attempted (See, e.g., Shrout et al. (2000) *J. Periodonol.* 71:335-340; Verhoeven et al. (1998) *Clin Oral Implants Res* 9(5):333-342), these have not provided accurate and reliable results.

Furthermore, current methods and devices do not generally take into account bone structure analyses. See, e.g., Ruttimann et al. (1992) *Oral Surg Oral Med Oral Pathol* 74:98-110; Southard & Southard (1992) *Oral Surg Oral Med Oral Pathol* 73:751-9; White & Rudolph, (1999) *Oral Surg Oral Med Oral Pathol Oral Radiol Endod* 88:628-35.

Thus, although a number of devices and methods exist for evaluating bone, there are a number of limitations on such devices and methods. Consequently, the inventors have recognized the need, among other things, to provide methods and compositions that result in the ability to obtain accurate bone mineral density and bone structure information from images (e.g., radiographic images) containing the bone and related subject data.

SUMMARY

In one aspect, the invention includes a method for analyzing bone structure or bone density, the method comprising the steps of: obtaining an image of a subject, wherein the image comprises an image of the subject's bone; estimating probable volumetric structure of bone; and measuring one or more parameters of estimated volumetric structure of bone. The image may be an MRI or an x-ray image. In certain embodiments, the parameter measured comprises structural strength.

In another aspect, the invention comprises a method for estimating fracture risk in a subject, the method comprising the steps of: obtaining an image of the subject, wherein the image comprises an image of the subject's bone; estimating probable volumetric structure of bone; measuring one or more parameters of estimated volumetric structure of bone; and comparing the measurements to measurements of population data, thereby estimating fracture risk in the subject.

In yet another aspect, the invention comprises a method for estimating future fracture risk in a subject, the method comprising the steps of: obtaining an image of the subject, wherein the image comprises an image of the subject's bone; estimating probable volumetric structure of bone; measuring bone quality parameters of estimated volumetric structure of bone; simulating bone remodeling using the estimated volumetric structure of bone; and comparing the bone quality measurements on resultant structures from simulation of bone remodeling to measurements of population data, thereby predicting future fracture risk in the subject under simulation conditions. In certain embodiment, the simulation of bone remodeling is of therapeutic interventions. In other embodiments, the simulation of bone remodeling is of disease progression.

In another aspect, the invention includes a method for monitoring the effect of an agent on bone quality and/or a system for drug discovery. The method generally comprises: (a) obtaining bone quality (e.g., bone density or bone structure) measurements on a subject, wherein the measurements are obtained using any of the methods described herein; (b) administering an agent to the subject; (c) obtaining bone quality (e.g., bone density or bone structure) measurements of the subject after administration of the agent, wherein the measurements are obtained using any of the methods described herein; and (d) comparing bone quality (e.g., bone density or bone structure) measurements from steps (a) and (c).

In various embodiments of the invention, one or more measurements pertaining to, without limitation, bone mineral density, bone architecture or structure, macro-anatomy, and/or bone biomechanics, may be generated from two or more x-ray beam rotation angles. The x-rays may be acquired, without limitation, by a conventional radiography unit, a conventional tomography unit (e.g., CT scan), or a digital radiography unit (e.g., digital radiography (DR) or computed radiography (CR) systems). If a DR or CR system is implemented, images may be obtained from multiple rotation angles so as to allow tomographic reconstruction.

In one aspect, the invention includes a method for analyzing bone. The method generally includes obtaining an image(s) of a subject by digital radiography (DR) and computed radiography (CR) over multiple x-ray beam rotation angles, wherein the image comprises an image of the subject's bone. One or more parameters are determined based, at least in part, on the image(s). The one or more parameters include at least one of a macroanatomical parameter, a biomechanical parameter, bone structure, structural strength, and bone mineral density.

In related embodiments, the one or more parameters determined may be compared to measurements of population data, thereby estimating fracture risk in the subject. These and other embodiments of the present invention will readily occur to those of ordinary skill in the art in view of the disclosure herein.

BRIEF DESCRIPTION OF THE DRAWINGS

FIG. 1A depicts no erosion (Level 0) and FIGS. 1A to I depict further erosions of each the previous panels (Levels 1 to 8).

FIG. 5, panels A and B, are graphs depicting relationships of measurements from projection vs. model density.

FIG. 6, panels A to D, depicts exemplary projections of rods and plates.

FIG. 7, panels A and B, are graphs depicting projection vs. 3D structure density.

FIG. 8, panels A and B, are graphs depicting simulated erosion.

FIG. 10, panels A to D, are graphs depicting various 2D parameters in simulated erosions.

DESCRIPTION

Figure 1:
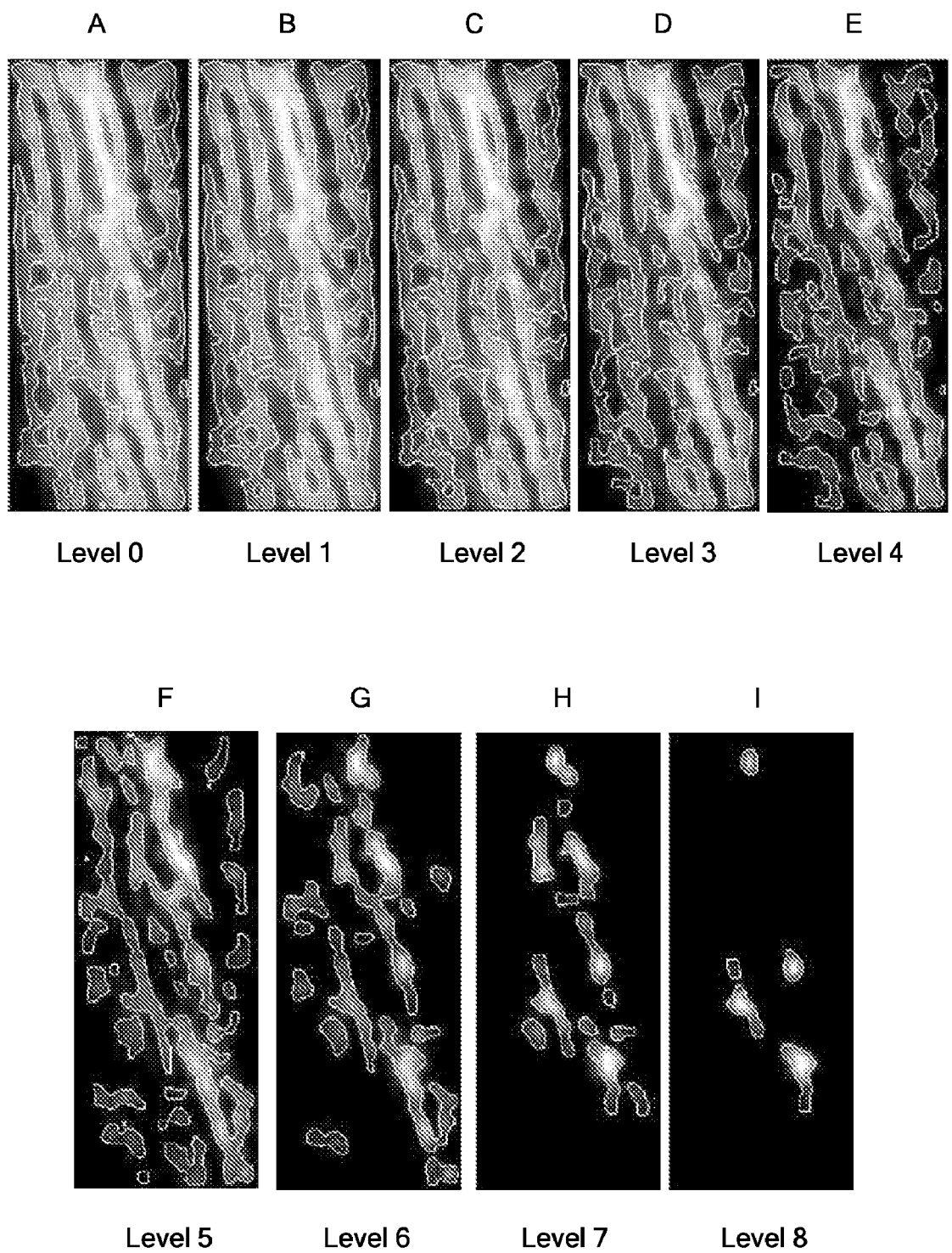
FIG. 1, panels A-I, are reproductions of various projections of volume images (uCT, MRI) when simulated remodeling techniques are applied.
Figure 2:
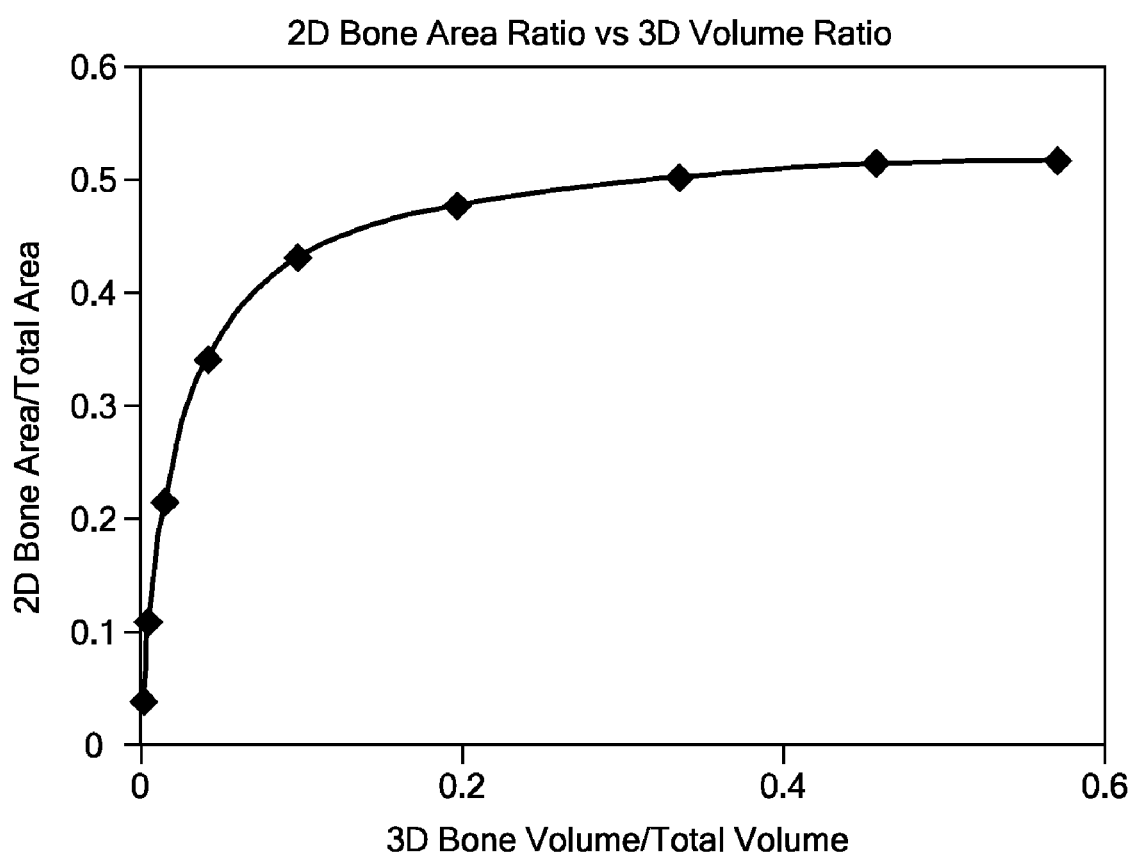
FIG. 2 is a graph depicting 2D bone area ratio measurements from various simulated bone remodeling levels versus corresponding 3 D volume ratio measurements.

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

The practice of the present invention employs, unless otherwise indicated, currently conventional methods of imaging and image processing within the skill of the art. Such techniques are explained fully in the literature. See, e.g., WO 02/22014, X-Ray Structure Determination: A Practical Guide, $2^{nd}$ Edition, editors Stout and Jensen, 1989, John Wiley & Sons, publisher; Body CT: A Practical Approach, editor Slone, 1999, McGraw-Hill publisher; The Essential Physics of Medical Imaging, editors Bushberg, Seibert, Leidholdt Jr & Boone, 2002, Lippincott, Williams & Wilkins; X-ray Diagnosis: A Physician's Approach, editor Lam, 1998 Springer-Verlag, publisher; Dental Radiology: Understanding the X-Ray Image, editor Laetitia Brocklebank 1997, Oxford University Press publisher; and Digital Image Processing, editor Kenneth R. Castleman, 1996 Prentice Hall, publisher; The Image Processing Handbook, editor John C. Russ, $3^{rd}$ Edition, 1998, CRC Press; Active Contours: The Application of Techniques from Graphics, Vision, Control Theory and Statistics to Visual Tracking of Shapes in Motion, Editors Andrew Blake, Michael Isard, 1999 Springer Verlag. As will be appreciated by those of skill in the art, as the field of imaging continues to advance methods of imaging currently employed can evolve over time. Thus, any imaging method or technique that is currently employed is appropriate for application of the teachings of this invention as well as techniques that can be developed in the future. A further detailed description of imaging methods is not provided in order to avoid obscuring the invention.

Described herein are methods for bone structure prognosis and simulated bone remodeling. Bone remodeling is a physiological process in which continuous bone resorption (loss) and bone formation (gain) occurs. When the bone resorption rate is higher than bone formation rate, a net bone loss occurs, thereby causing an overall reduction of bone mass and quality. Conversely, when bone formation rate is higher than the resorption rate, a net bone gain occurs. Using the techniques described herein, bone loss or bone gain can be simulated in any given subject. In addition, the efficacy of drug therapy can be validated, putative drugs or therapies can be evaluated, and better models can be obtained for bone loss. The methods described herein also allow for the generation of non-linear mathematical relationships for the bone loss and gain models as well as improved methods of predicting progression of disease.

In certain embodiments the methods involve estimation of 3D structures or measurement values of the equivalent 3D, from 2D projection radiographs. Subsequently, the methods involve generating an extrapolation of bone degradation or growth from one or more projection radiographs or 3D images (μCT, mri). This mathematical extrapolation is typically based on characterization of bone loss or growth trends of one or more sampling of images and other relevant patient information. For instance, a trend characterization can involve using measurements of microstructure and macro-anatomical parameters such as trabecular area ratio, trabecular thickness, cortical bone thickness and patient information such as age, gender, and ethnicity. The extrapolation calculation can be based on mathematical modeling of the physiology of bone remodeling using methods such as Monte-Carlo simulation, stochastic methods or artificial neural networks.

Using the techniques described herein, a correlation can be made between 3D trabecular volumetric measurements and 2D trabecular measurements. The relationship between these two measurements can be determined as a mathematical relationship that is non-linear, e.g. curvilinear, exponential, logarithmic, etc. Obtaining the mathematical relationship enables a more accurate simulation and enables thresholds to be calculated more accurately. Once the method to simulate bone loss is developed, it can be used to evaluate (measure) bone structure over time. From this a rate of erosion of bone loss can be modeled and, accordingly, a user can calibrate bone loss in the model that takes into consideration conditions present in actual population data. Once two data points are obtained for any patient, those data points can be compared to the population data to determine the likely rate of loss for that patient and to predict when a fracture would be likely to occur.

The first step is to locate a bone in the body of a subject, for example in a human body, for study. Once the bone is selected, an image or a series of images including the particular selected bone, e.g. hip, dental, spine, etc. are acquired. Images include, for example, conventional x-ray images, x-ray tomosynthesis, ultrasound (including A-scan, B-scan and C-scan) computed tomography (CT scan), magnetic resonance imaging (MRI), optical coherence tomography, single photon emission tomography (SPECT), and positron emission tomography, or such other imaging tools that a person of skill in the art would find useful in practicing the invention.

Once the image is taken, 3D structural representations can be generated from the data in the image, for example in a region of interest (ROI) located within the image. Algorithms can be used to automatically place regions of interest in a particular image. The quantitative and/or qualitative data extracted from the image and used to generate 3D structural prediction(s) includes, for example, the parameters and measurements shown in Table 1, Table 2 or Table 3.

Each step of locating a part of the body for study, optionally locating a region of interest, obtaining image data, and deriving data, can be repeated one or more times, respectively, as desired.

Image data can be optionally enhanced by applying image processing techniques, such as noise filtering or diffusion filtering, to facilitate further analysis.

TABLE 1

Representative Parameters Measured with
Quantitative and Qualitative Image Analysis Methods

| PARAMETER | MEASUREMENTS |
|---|---|
| Bone density and microstructural parameters | Calibration phantom equivalent thickness (Average intensity value of the region of interest expressed as thickness of calibration phantom that would produce the equivalent intensity) |
| | Trabecular contrast |
| | Standard deviation of background subtracted ROI |
| | Coefficient of Variation of ROI (Standard deviation/mean) |
| | (Trabecular equivalent thickness/Marrow equivalent thickness) |
| | Fractal dimension |
| | Hough transform |
| | Fourier spectral analysis |
| | (Mean transform coefficient absolute value and mean spatial first moment) |
| | Predominant orientation of spatial energy spectrum |
| | Trabecular area |
| | (Pixel count of extracted trabeculae) |
| | Trabecular area/Total area |
| | Trabecular perimeter |
| | (Count of trabecular pixels with marrow pixels in their neighborhood, proximity or vicinity) |
| | Trabecular distance transform |
| | (For each trabecular pixel, calculation of distance to closest marrow pixel) |
| | Marrow distance transform |
| | (For each marrow pixel, calculation of distance to closest trabecular pixel) |
| | Trabecular distance transform regional maximal values (mean, min., max, std. Dev). |
| | (Describes thickness and thickness variation of trabeculae) |
| | Marrow distance transform regional maximal values (mean, min., max, std. Dev) |
| | Star volume |
| | (Mean volume of all the parts of an object which can be seen unobscured from a random point inside the object in all possible directions) |
| | Trabecular Bone Pattern Factor |
| | (TBPf = (P1 − P2)/(A1 − A2) where P1 and A1 are the perimeter length and trabecular bone area before dilation and P2 and A2 corresponding values after a single pixel dilation, measure of connectivity) |
| | Connected skeleton count or Trees (T) |
| | Node count (N) |
| | Segment count (S) |
| | Node-to-node segment count (NN) |
| | Node-to-free-end segment count (NF) |
| | Node-to-node segment length (NNL) |
| | Node-to-free-end segment length (NFL) |
| | Free-end-to-free-end segment length (FFL) |
| | Node-to-node total struts length (NN.TSL) |
| | Free-end-to-free-ends total struts length(FF.TSL) |
| | Total struts length (TSL) |
| | FF.TSL/TSL |
| | NN.TSL/TSL |
| | Loop count (Lo) |
| | Loop area |
| | Mean distance transform values for each connected skeleton |
| | Mean distance transform values for each segment (Tb.Th) |
| | Mean distance transform values for each node-to-node segment (Tb.Th.NN) |
| | Mean distance transform values for each node-to-free-end segment (Tb.Th.NF) |
| | Orientation (angle) of each segment |
| | Angle between segments |
| | Length-thickness ratios (NNL/Tb.Th.NN) and (NFL/Tb.Th.NF) |
| | Interconnectivity index (ICI) |
| | ICI = (N * NN)/(T * (NF + 1)) |
| Cartilage and cartilage defect/diseased cartilage parameters | Total cartilage volume |
| | Partial/Focal cartilage volume |
| | Cartilage thickness distribution (thickness map) |
| | Mean cartilage thickness for total region or focal region |
| | Median cartilage thickness for total region or focal region |
| | Maximum cartilage thickness for total region or focal region |
| | Minimum cartilage thickness for total region or focal region |
| | 3D cartilage surface information for total region or focal region |
| | Cartilage curvature analysis for total region or focal region |
| | Volume of cartilage defect/diseased cartilage |
| | Depth of cartilage defect/diseased cartilage |
| | Area of cartilage defect/diseased cartilage |
| | 2D or 3D location of cartilage defect/diseased cartilage in articular surface |
| | 2D or 3D location of cartilage defect/diseased cartilage in relationship to weight-bearing area |
| | Ratio: diameter of cartilage defect or diseased cartilage/thickness of surrounding normal cartilage |
| | Ratio: depth of cartilage defect or diseased cartilage/thickness of surrounding normal cartilage |
| | Ratio: volume of cartilage defect or diseased cartilage/thickness of surrounding normal cartilage |
| | Ratio: surface area of cartilage defect or diseased cartilage/total joint or articular surface area |
| | Ratio: volume of cartilage defect or diseased cartilage/total cartilage volume |
| Other articular parameters | Presence or absence of bone marrow edema |
| | Volume of bone marrow edema |
| | Volume of bone marrow edema normalized by width, area, size, volume of femoral condyle(s)/tibial plateau/patella - other bones in other joints |
| | Presence or absence of osteophytes |
| | Presence or absence of subchondral cysts |
| | Presence or absence of subchondral sclerosis |
| | Volume of osteophytes |
| | Volume of subchondral cysts |
| | Volume of subchondral sclerosis |
| | Area of bone marrow edema |
| | Area of osteophytes |
| | Area of subchondral cysts |
| | Area of subchondral sclerosis |
| | Depth of bone marrow edema |
| | Depth of osteophytes |
| | Depth of subchondral cysts |
| | Depth of subchondral sclerosis |
| | Volume, area, depth of osteophytes, subchondral cysts, subchondral sclerosis normalized by width, area, size, volume of femoral condyle(s)/tibial plateau/patella - other bones in other joints |
| | Presence or absence of meniscal tear |
| | Presence or absence of cruciate ligament tear |
| | Presence or absence of collateral ligament tear |
| | Volume of menisci |
| | Ratio of volume of normal to torn/damaged or degenerated meniscal tissue |
| | Ratio of surface area of normal to torn/damaged or degenerated meniscal tissue |
| | Ratio of surface area of normal to torn/damaged or degenerated meniscal tissue to total joint or cartilage surface area |
| | Ratio of surface area of torn/damaged or degenerated meniscal tissue to total joint or cartilage surface area |
| | Size ratio of opposing articular surfaces |
| | Meniscal subluxation/dislocation in mm |
| | Index combining different articular parameters which can also include |
| | Presence or absence of cruciate or collateral ligament tear |

TABLE 1-continued

Representative Parameters Measured with
Quantitative and Qualitative Image Analysis Methods

| PARAMETER | MEASUREMENTS |
|---|---|
| | Body mass index, weight, height |
| | 3D surface contour information of subchondral bone |
| | Actual or predicted knee flexion angle during gait cycle (latter based on gait patterns from subjects with matching demographic data retrieved from motion profile database) |
| | Predicted knee rotation during gait cycle |
| | Predicted knee displacement during gait cycle |
| | Predicted load bearing line on cartilage surface during gait cycle and measurement of distance between load bearing line and cartilage defect/diseased cartilage |
| | Predicted load bearing area on cartilage surface during gait cycle and measurement of distance between load bearing area and cartilage defect/diseased cartilage |
| | Predicted load bearing line on cartilage surface during standing or different degrees of knee flexion and extension and measurement of distance between load bearing line and cartilage defect/diseased cartilage |
| | Predicted load bearing area on cartilage surface during standing or different degrees of knee flexion and extension and measurement of distance between load bearing area and cartilage defect/diseased cartilage |
| | Ratio of load bearing area to area of cartilage defect/diseased cartilage |
| | Percentage of load bearing area affected by cartilage disease |
| | Location of cartilage defect within load bearing area |
| | Load applied to cartilage defect, area of diseased cartilage |
| | Load applied to cartilage adjacent to cartilage defect, area of diseased cartilage |

TABLE 2

Site specific measurement of bone parameters

| | |
|---|---|
| Parameters specific to hip images | All microarchitecture parameters on structures parallel to stress lines |
| | All microarchitecture parameters on structures perpendicular to stress lines |
| | Geometry |
| | Shaft angle |
| | Neck angle |
| | Average and minimum diameter of femur neck |
| | Hip axis length |
| | CCD (caput-collum-diaphysis) angle |
| | Width of trochanteric region |
| | Largest cross-section of femur head |
| | Standard deviation of cortical bone thickness within ROI |
| | Minimum, maximum, mean and median thickness of cortical bone within ROI |
| | Hip joint space width |
| Parameters specific to spine images | All microarchitecture parameters on vertical structures |
| | All microarchitecture parameters on horizontal structures |
| | Geometry |
| | Superior endplate cortical thickness (anterior, center, posterior) |
| | Inferior endplate cortical thickness (anterior, center, posterior) |
| | Anterior vertebral wall cortical thickness (superior, center, inferior) |
| | Posterior vertebral wall cortical thickness (superior, center, inferior) |
| | Superior aspect of pedicle cortical thickness inferior aspect of pedicle cortical thickness |
| | Vertebral height (anterior, center, posterior) |

TABLE 2-continued

Site specific measurement of bone parameters

| | |
|---|---|
| | Vertebral diameter (superior, center, inferior), Pedicle thickness (supero-inferior direction). |
| | Maximum vertebral height |
| | Minimum vertebral height |
| | Average vertebral height |
| | Anterior vertebral height |
| | Medial vertebral height |
| | Posterior vertebral height |
| | Maximum inter-vertebral height |
| | Minimum inter-vertebral height |
| | Average inter-vertebral height |
| Parameters specific to knee images | Average medial joint space width |
| | Minimum medial joint space width |
| | Maximum medial joint space width |
| | Average lateral joint space width |
| | Minimum lateral joint space width |
| | Maximum lateral joint space width |

TABLE 3

Measurements applicable on Microarchitecture and Macro-anatomical Structures

| | |
|---|---|
| Average density measurement | Calibrated density of ROI |
| Measurements on micro-anatomical structures of dental, spine, hip, knee or bone cores images | The following parameters are derived from the extracted structures: |
| | Calibrated density of extracted structures |
| | Calibrated density of background |
| | Average intensity of extracted structures |
| | Average intensity of background (area other than extracted structures) |
| | Structural contrast (average intensity of extracted structures/average intensity of background) |
| | Calibrated structural contrast (calibrated density extracted structures/calibrated density of background) |
| | Total area of extracted structures |
| | Total area of ROI |
| | Area of extracted structures normalized by total area of ROI |
| | Boundary lengths (perimeter) of extracted normalized by total area of ROI |
| | Number of structures normalized by area of ROI |
| | Trabecular bone pattern factor; measures concavity and convexity of structures |
| | Star volume of extracted structures |
| | Star volume of background |
| | Number of loops normalized by area of ROI |
| Measurements on Distance transform of extracted structures | The following statistics are measured from the distance transform regional maximum values: |
| | Average regional maximum thickness |
| | Standard deviation of regional maximum thickness |
| | Largest value of regional maximum thickness |
| | Median of regional maximum thickness |
| Measurements on skeleton of extracted structures | Average length of networks (units of connected segments) |
| | Maximum length of networks |
| | Average thickness of structure units (average distance transform values along skeleton) |
| | Maximum thickness of structure units (maximum distance transform values along skeleton) |
| | Number of nodes normalized by ROI area |
| | Number of segments normalized by ROI area |
| | Number of free-end segments normalized by ROI area |
| | Number of inner (node-to-node) segments normalized ROI area |
| | Average segment lengths |
| | Average free-end segment lengths |
| | Average inner segment lengths |
| | Average orientation angle of segments |
| | Average orientation angle of inner segments |
| | Segment tortuosity; a measure of straightness |
| | Segment solidity; another measure of straightness |

TABLE 3-continued

Measurements applicable on Microarchitecture and Macro-anatomical Structures

| | |
|---|---|
| | Average thickness of segments (average distance transform values along skeleton segments) |
| | Average thickness of free-end segments |
| | Average thickness of inner segments |
| | Ratio of inner segment lengths to inner segment thickness |
| | Ratio of tree-end segment lengths to tree-end segment thickness |
| | Interconnectivity index; a function of number of inner segments, free-end segments and number of networks. |
| Directional skeleton segment measurements | All measurement of skeleton segments can be constrained by one or more desired orientation by measuring only skeleton segments within ranges of angle. |
| Watershed segmentation | Watershed segmentation is applied to gray level images. |
| | Statistics of watershed segments are: |
| | Total area of segments |
| | Number of segments normalized by total area of segments |
| | Average area of segments |
| | Standard deviation of segment area |
| | Smallest segment area |
| | Largest segment area |

As will be appreciated by those of skill in the art, the parameters and measurements shown in Tables 1, 2 and 3 are provided for illustration purposes and are not intended to be limiting. It will be apparent that the terms micro-structural parameters, micro-architecture, micro-anatomic structure, micro-structural and trabecular architecture may be used interchangeably. In addition, other parameters and measurements, ratios, derived values or indices can be used to extract quantitative and/or qualitative information without departing from the scope of the invention. See, e.g., co-owned International Application WO 02/30283.

Extracted structures typically refer to simplified or amplified representations of features derived from images. An example would be binary images of trabecular patterns generated by background subtraction and thresholding. Another example would be binary images of cortical bone generated by applying an edge filter and thresholding. The binary images can be superimposed on gray level images to generate gray level patterns of structure of interest.

Figure 3:
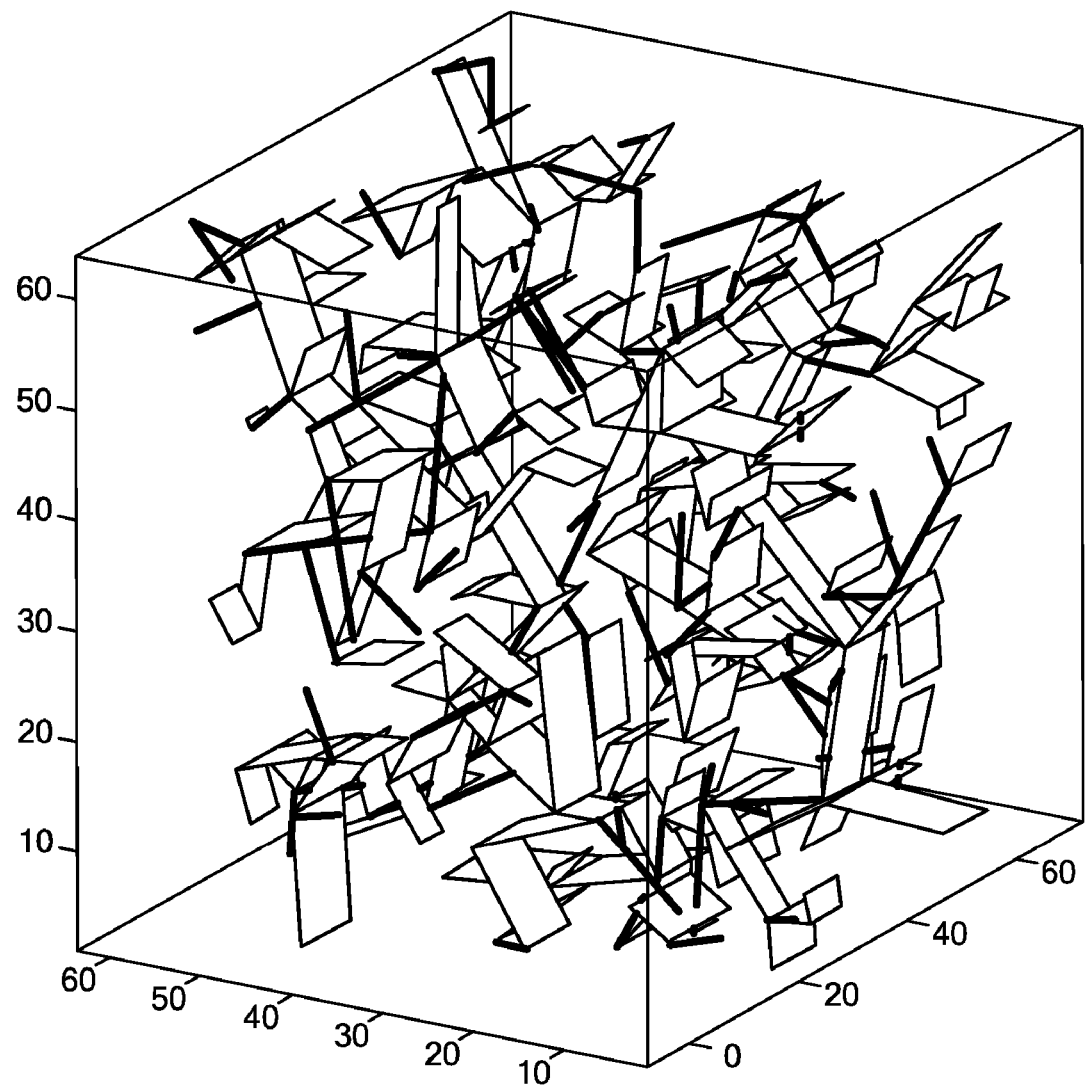
FIG. 3 is a schematic diagram depicting an exemplary configuration of rods and plates generated with a model to simulate a stage of bone growth.
Figure 4A:
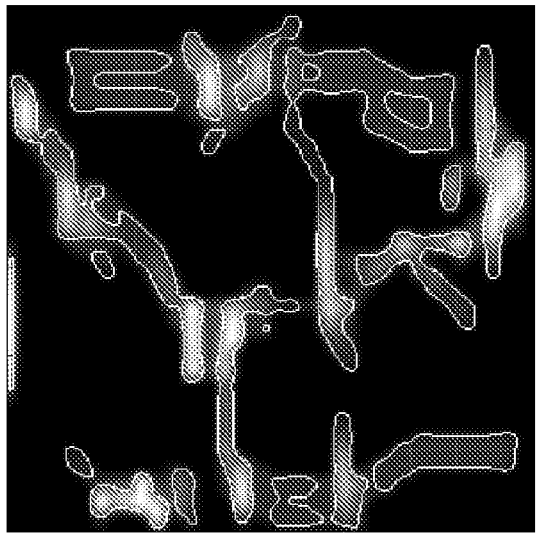
FIG. 4, panels A-D, depict projections and structure extraction of simulated bone growth in vertebra with various configurations of rod and plate trabecular bone.
Figure 4B:
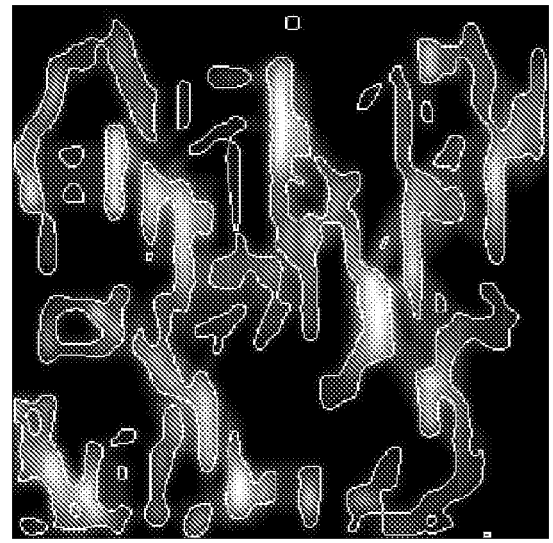
Figure 4C:
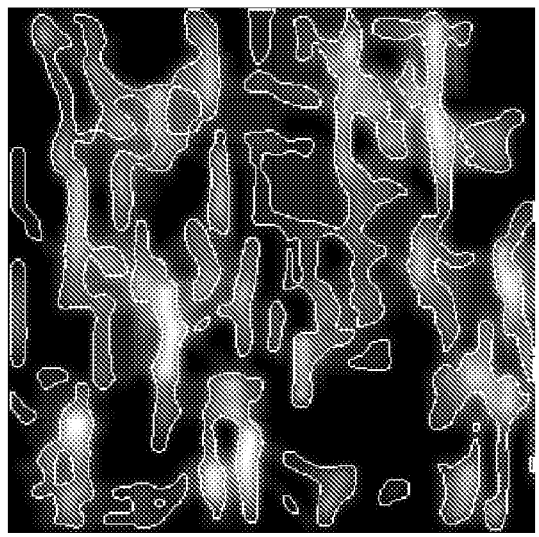
Figure 4D:
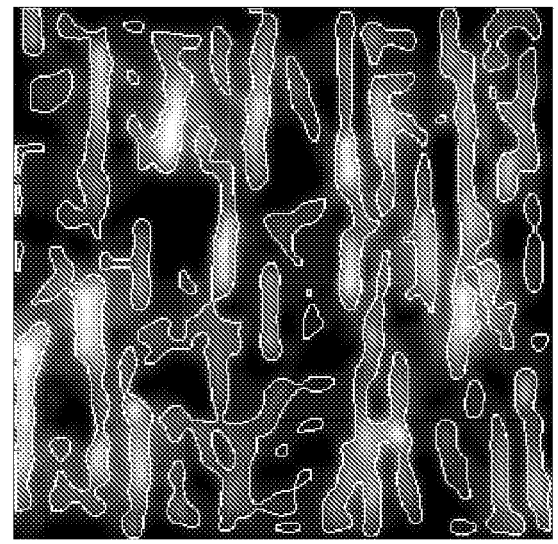
Figure 5A:
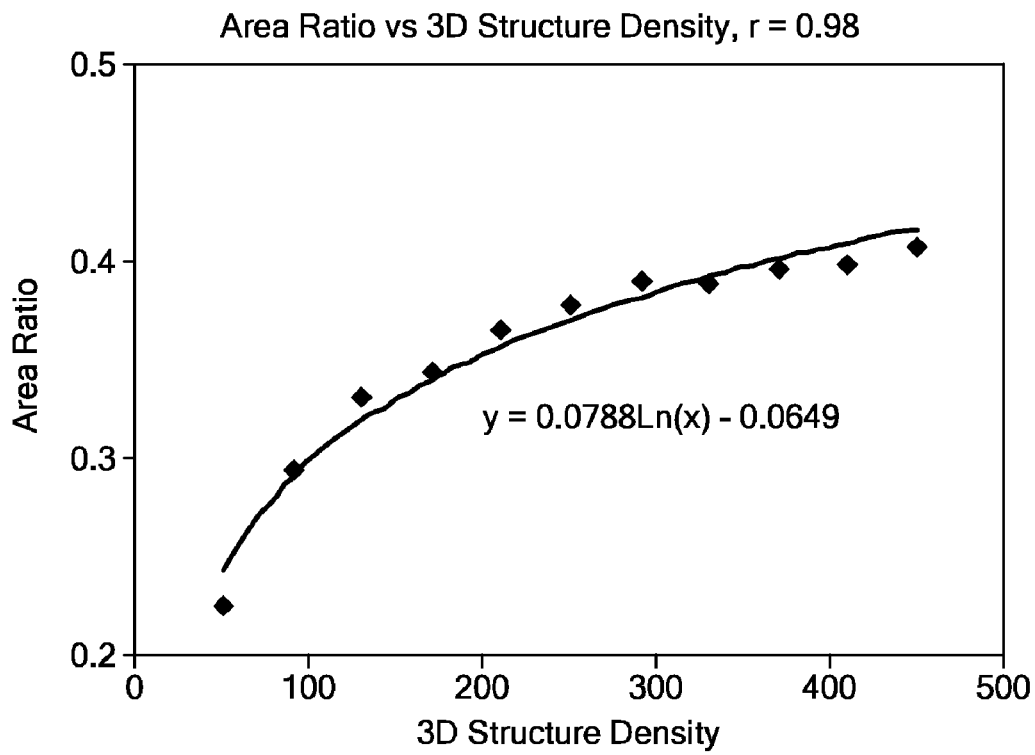
FIG. 5A depicts area ratio vs 3D structure density.
Figure 5B:
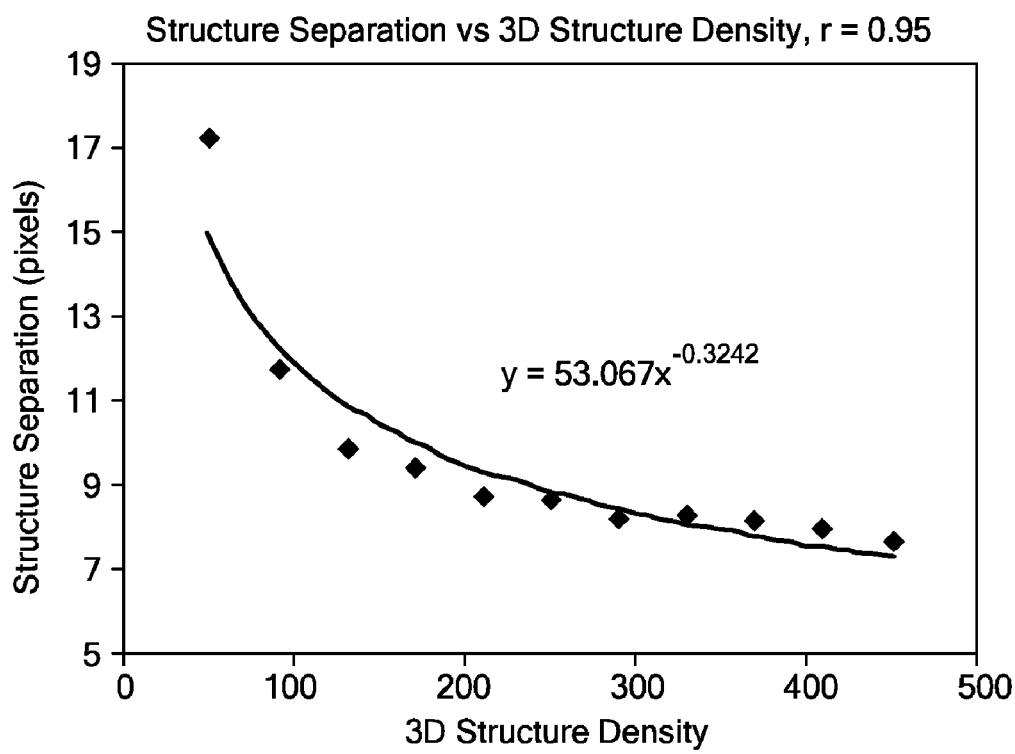
FIG. 5B depicts structure separation versus 3D structure density.
Figure 6A:
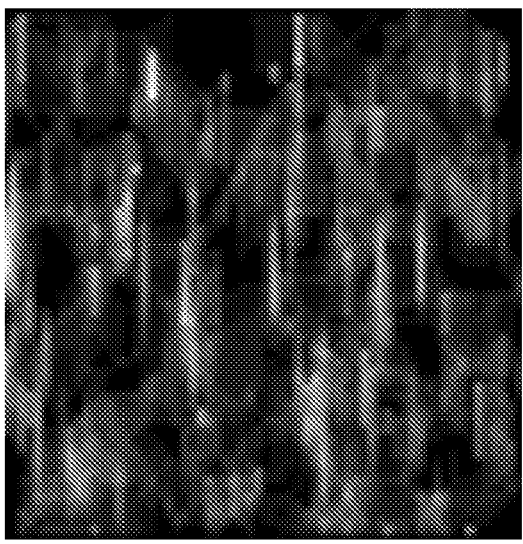
FIGS. 6A and 6B are projections at model density 410.
Figure 6B:
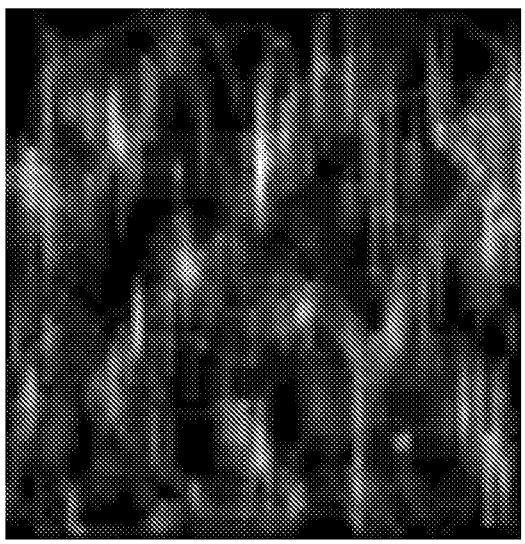
Figure 6C:
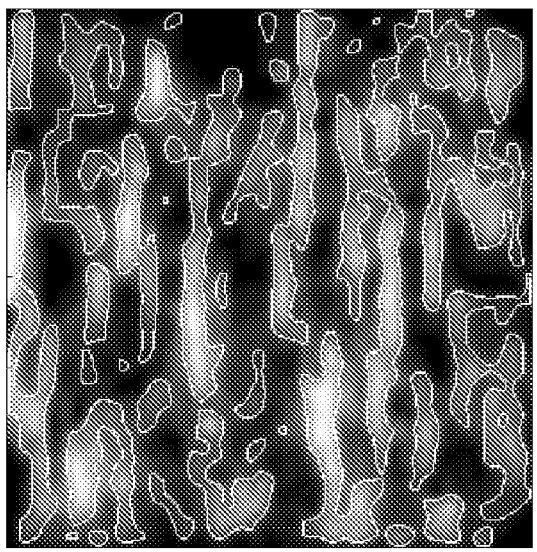
FIGS. 6C and 6D are projections at model density 450.
Figure 6D:
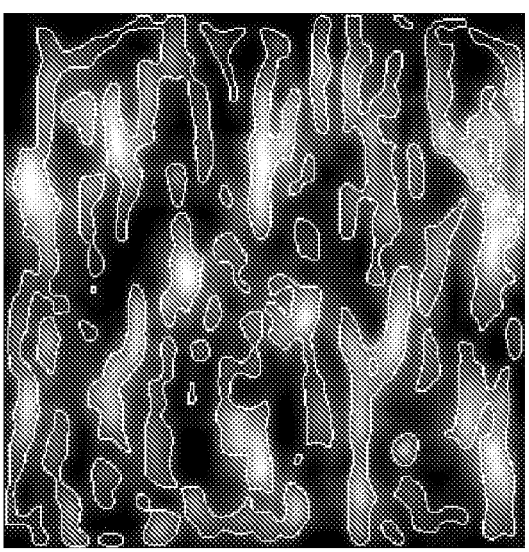
Figure 7A:
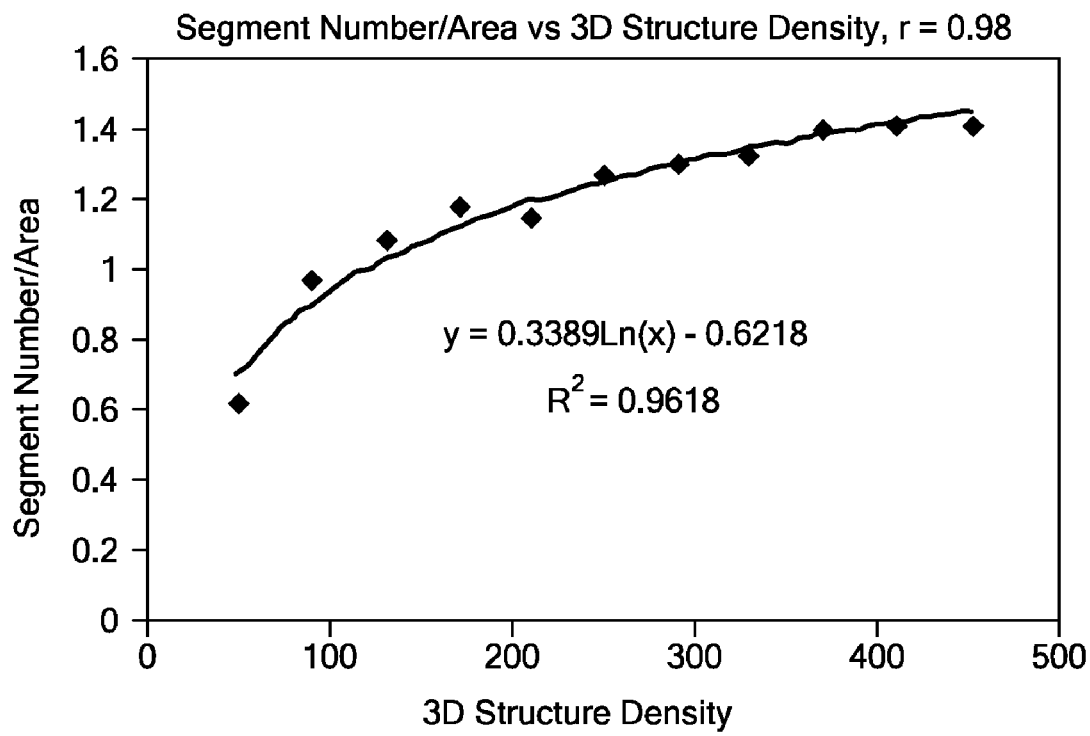
FIG. 7A depicts segment number/area vs. 3D structure density.
Figure 7B:
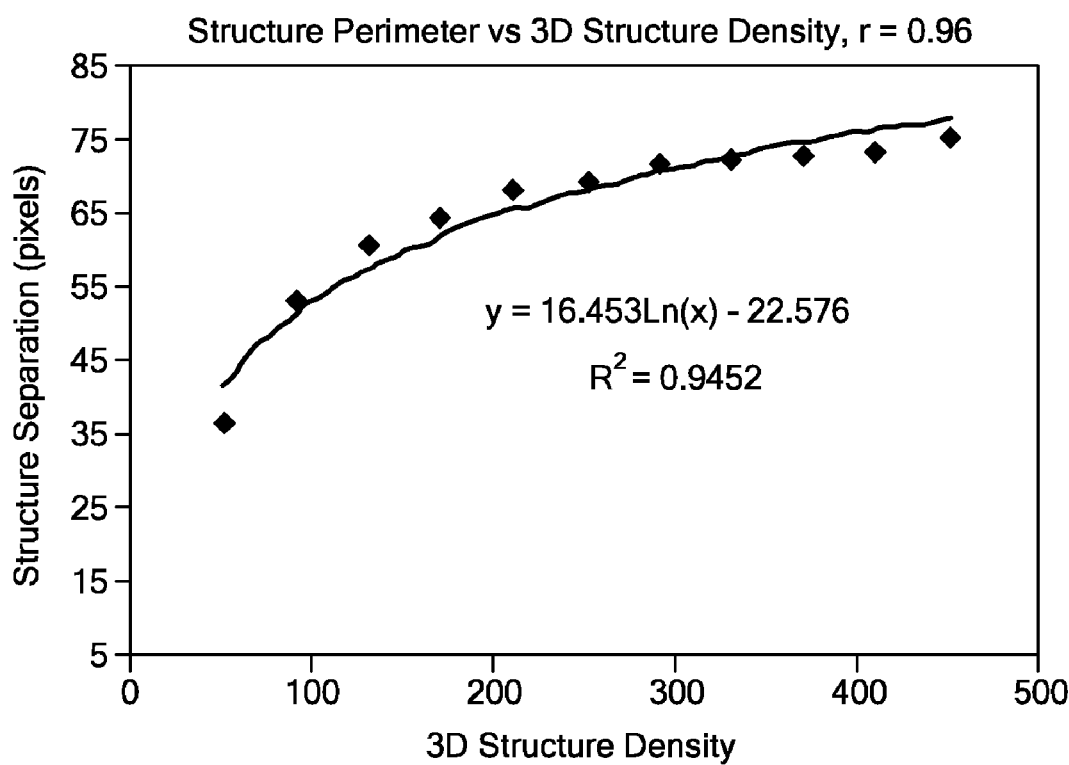
FIG. 7B depicts structure perimeter vs. 3D structure density.
Figure 8A:
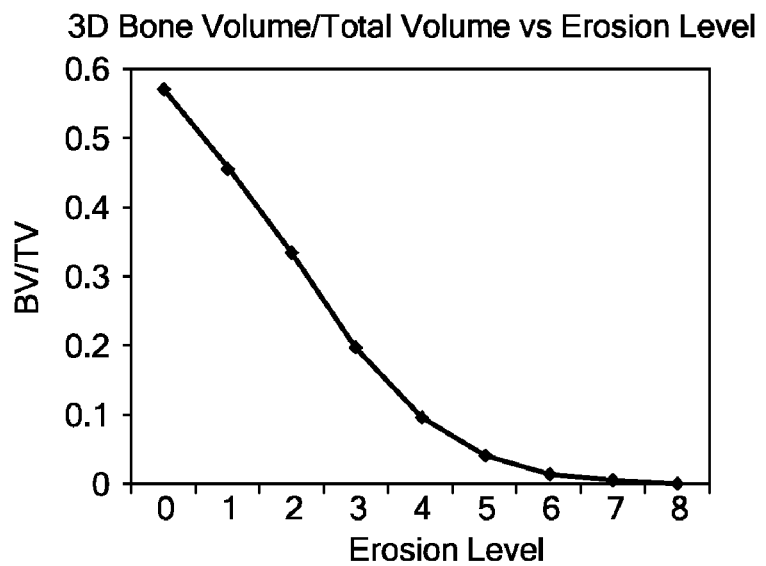
FIG. 8A depicts 3D bone volume/total volume vs. erosion level.
Figure 8B:
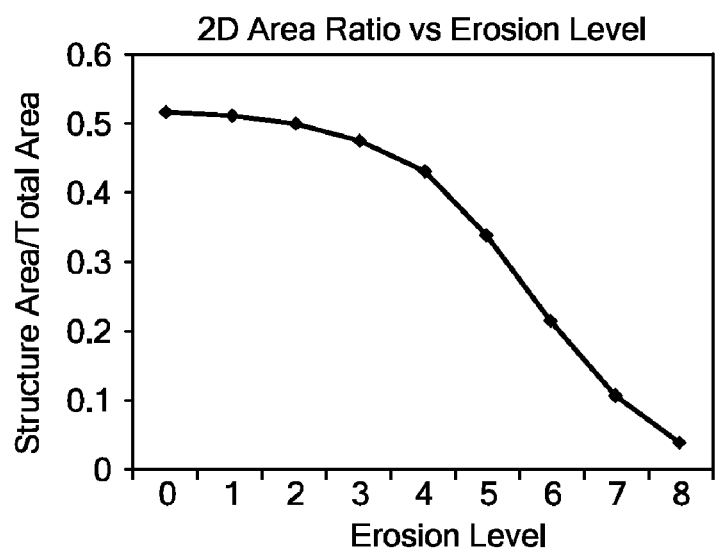
FIG. 8B depicts 2D area ratio vs. erosion level.
Figure 9:
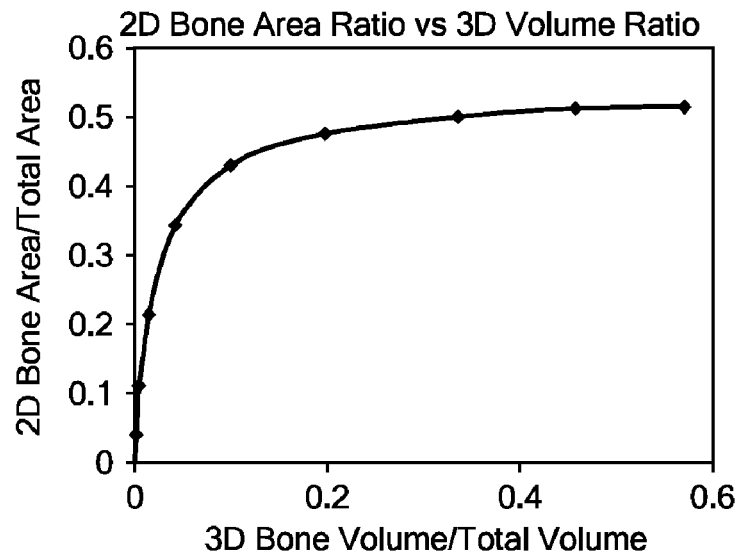
FIG. 9 is a graph depicting 2D bone area ratio vs. 3D volume ratio.
Figure 10A:
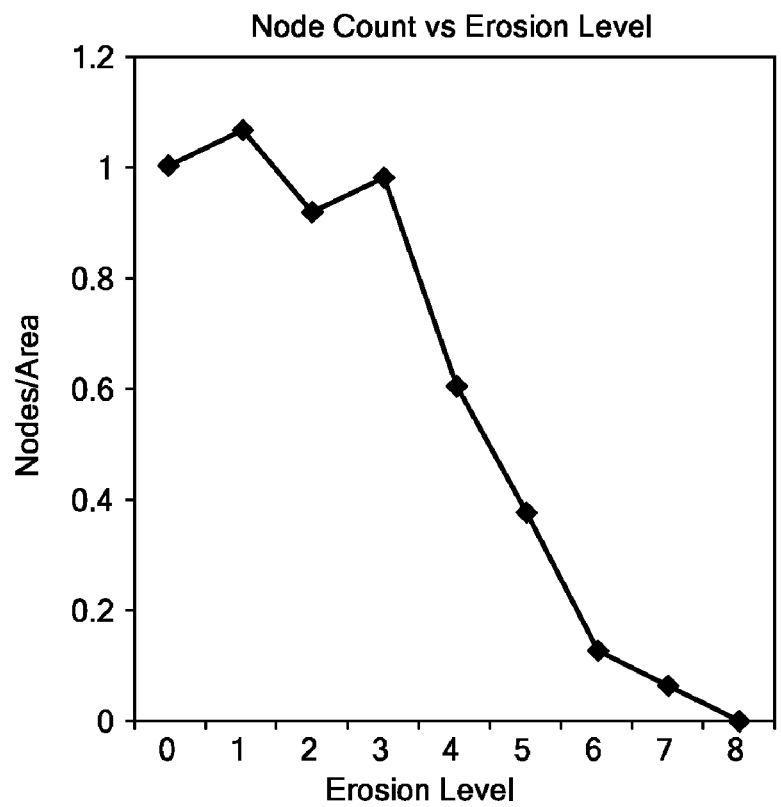
FIG. 10A depicts node count versus erosion level.
Figure 10B:
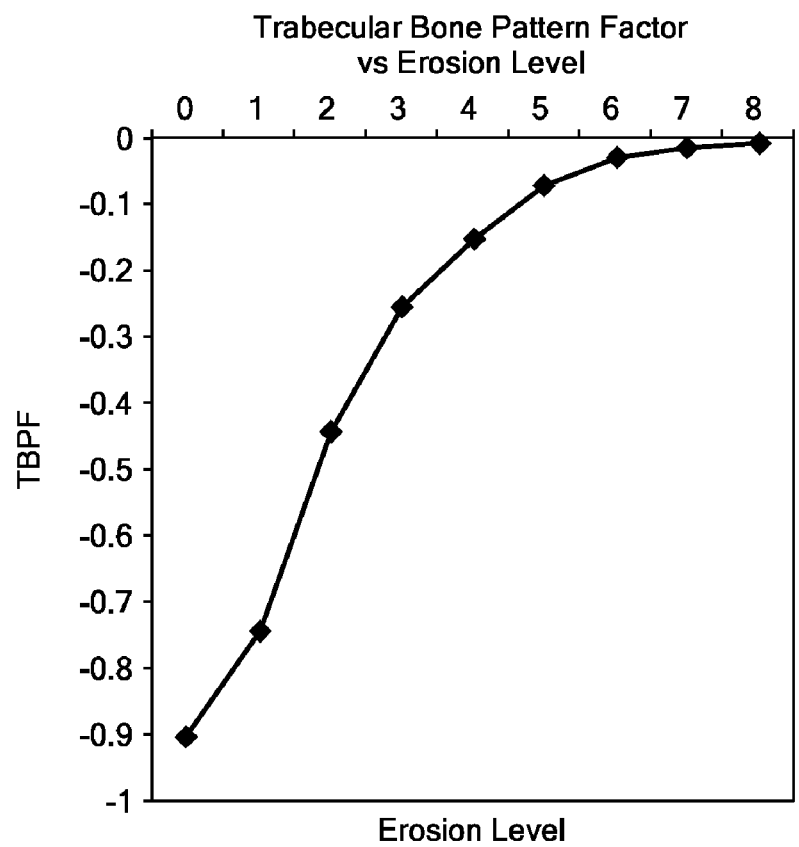
FIG. 10B depicts trabecular bone pattern factor vs. erosion level.
Figure 10C:
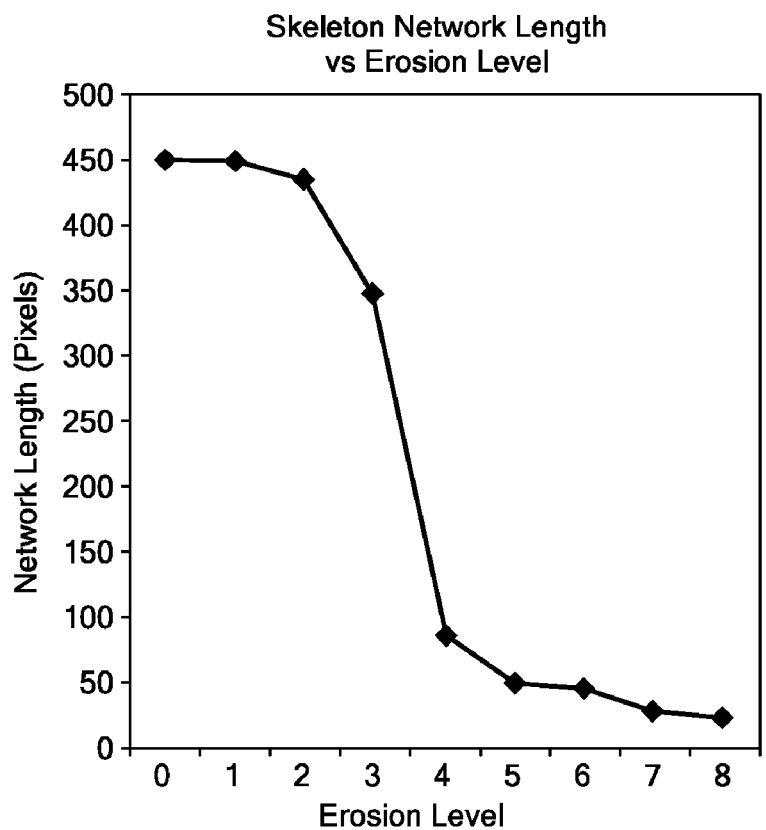
FIG. 10C depicts skeleton network length vs. erosion level.
Figure 10D:
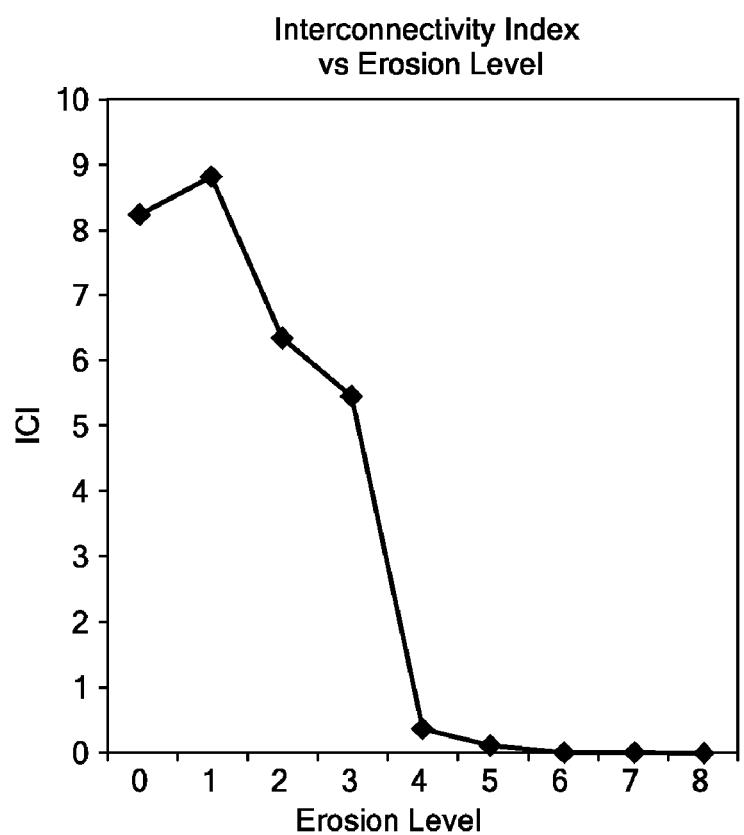
FIG. 10D depicts interconnectivity index vs. erosion level.

FIG. 1 shows an extrapolation of bone loss as generated from a 2D image of spine. Serial erosions are conducted on the image. An estimate of the most likely (e.g. maximum likelihood (non-Bayesian, classical approach) or maximum a-posteriori (Bayesian approach)) model for the volumetric structure that resulted in the 2-D projection structure shown in FIG. 1 can be achieved and is shown in FIG. 3.

Once the most likely 3-D structure model is obtained (e.g. FIG. 3) the corresponding 3-D parameters, which are easier to understand and more intuitive to analyze, can be used. In the event that it is determined that these parameters do not correlate well, additional parameters can be included. Thus a combination of 2D and 3D parameters can be used. Additionally, a family of models can be obtained from, for example, the 2-D structure of FIG. 1.

Specifically, staging or progression can be estimated by associating growth models to the nodes, rods and plates according to what is known about how a specific treatment affects these specific structures. For example, if a specific treatment is supposed to increase mineral deposition on the volume, the mineral diffusion from the blood rich regions towards the rest of the volume can be used to predict increase or decrease of density at several different stages.

Figure 11:
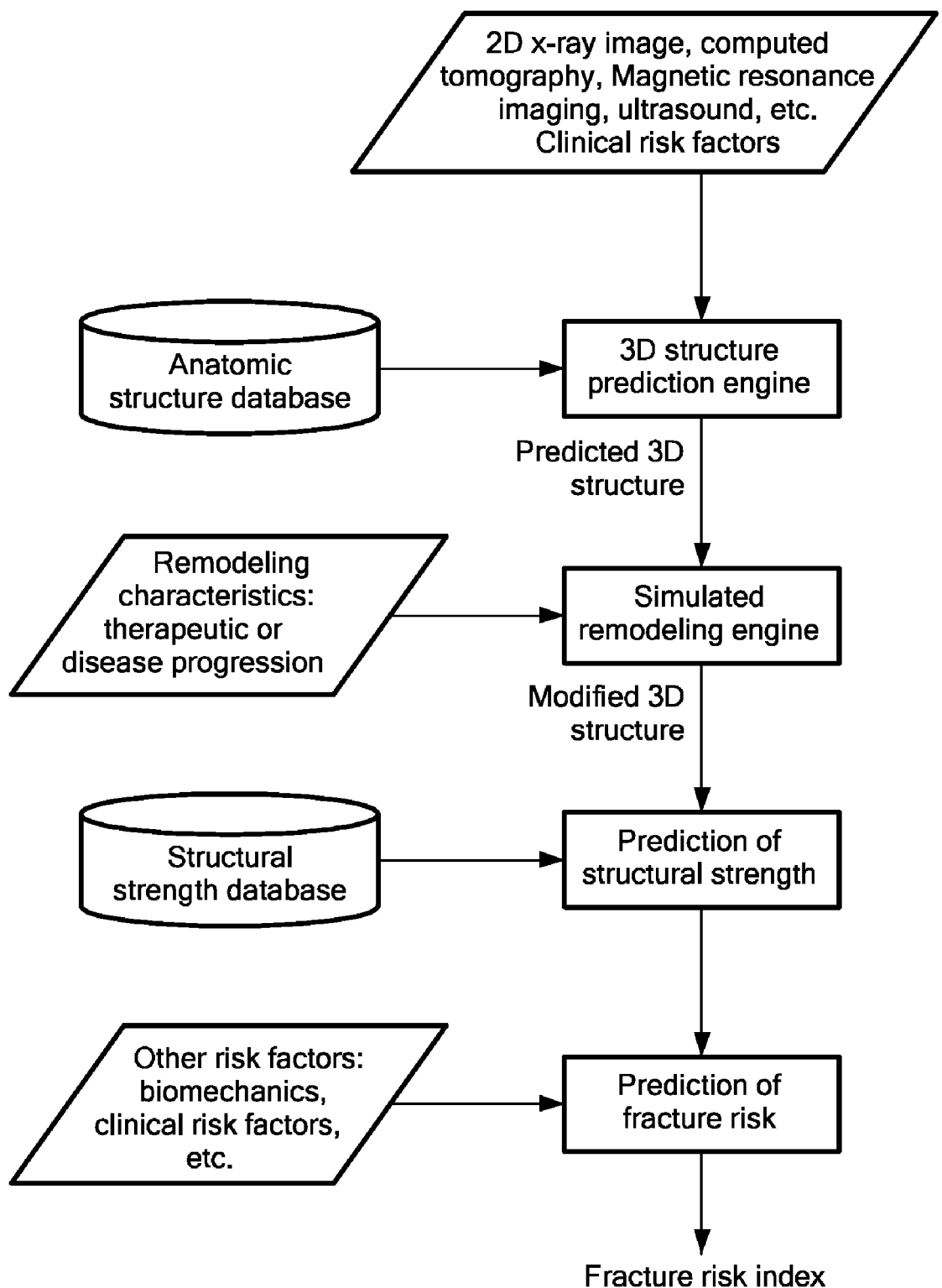
FIG. 11 is a schematic flowchart depicting various steps involved in an exemplary method of bone structure prognosis and simulated bone remodeling.

The flowchart shown in FIG. 11 depicts exemplary steps and information that can be used to predict fracture risk and/or generate a fracture risk index. A 2D digital image (e.g., digitized radiographs, digital detector radiograph, etc.) including bone is taken using standard techniques and a 3D structure prediction engine generates the most probable 3D structure given the 2D image. Optionally, a-priori knowledge of the most probable 3D structure in various regions of bones stored in an anatomic structure database, may be used to predict the 3D structure using techniques such as (including but not limited to) Bayesian inference methods, Monte Carlo simulations, artificial neural networks, etc. The anatomic structure database may contain probabilistic or functional models, numerical characteristics and 2D and/or 3D images of bone structures of various regions of bones.

Simulated remodeling is then applied to the predicted 3D structure, optionally using one or more remodeling characteristics of therapeutic interventions and/or or disease progression. The simulated bone remodeling engine generates the outcome of bone structure due to therapeutic interventions and/or disease progression at one or more time intervals. The remodeling characteristics can include data such as bone resorption and formation rates, measurements of hormonal levels, age, etc. Techniques such as morphological operations in combination with stochastic methods, Monte-Carlo simulations, artificial neural networks, etc, and be use to simulate bone remodeling. Optionally, a database containing a collection of bone remodeling characteristics of various therapeutics intervention modalities (chemical, physical, electromagnetic radiation, etc), and various stages of disease progression can be maintained to be used as reference sources for therapeutic specific or disease condition specific remodeling simulations.

Following remodeling of the predicted 3D structure, structure strength may be predicted using computational biomechanics modeling methods such as finite element analysis, curved bean model simulations, etc. on the 3D structures and/or on reprojected 2D structures. Optionally, the 2D and/or 3D structures can be analyzed to obtain the parameters described in Tables 1, 2, and 3. These parameters are subsequently used to predict structural strength by referencing to one or more structural strength databases. The databases may contain information that relate the measured structure parameters to structural strength.

Finally, fracture risk can be predicted as a fracture risk index generated in terms of the predicted structural strength, and optionally, in combination with other risk factors.

In various embodiments of the invention, one or more measurements pertaining to, without limitation, bone mineral density, bone architecture or structure, macro-anatomy, and/or bone biomechanics, may be generated from two or more x-ray beam rotation angles. The x-rays may be generated, without limitation, by a conventional radiography unit, a conventional tomography unit (CT scan), or a digital radiography unit (e.g., digital radiography (DR) or computed radiography (CR) systems) (see, for example, The Essential Physics of Medical Imaging, editors Bushberg, Seibert, Leidholdt Jr & Boone, 2002, Lippincott, Williams & Wilkins, incorporated herein by reference in its entirety). If a DR or CR system is implemented, images may be obtained from multiple rotation angles so as to allow tomographic reconstruction.

The use of multiple x-ray beam rotation angles advantageously may be used to identify anatomical landmarks more reliably. Reproducibility may be improved. Furthermore, the use of multiple x-ray beam rotation angles may be used for semi or true three-dimensional and/or volume assessments.

A combination of the above-described parameters (i.e., bone mineral density, bone architecture or structure, macro-anatomy, and bone biomechanics) may be assessed in two-dimensions and/or three-dimensions to determine, without limitation, a patient's bone fracture risk.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLES

Example 1

FEA Analysis of Bone Strength Based of Projection of Bone Remodeling for Prediction of Fracture Risk A fracture risk index is created for a specific patient following the steps outlined in FIG. 11 and shown to the patient to illustrate the condition of their bone(s) at a projected time in the future, for example 2 years, thereby demonstrating the bone loss that may occur without intervention (e.g., treatment).

In one example, the projected model can be used to advise a patient, for example, that after taking a particular treatment course of action the bone would be projected to look like A, whereas failing to treat the bone, the bone would degenerate to B. Thus providing an aid to illustrate and explain to patients different treatment options and how they would reflect in terms of the risk of having a fracture. For example, the model could be used to show that a treatment course could reduce fracture risk by 50% whereas non-treatment increases the fracture risk by, for example, 80%.

What is claimed is:

1. A method for analyzing bone structure or bone density using a computer system, the method comprising the steps of:
    (a) obtaining two-dimensional image data of at least a portion of a subject's bone including trabecular bone, wherein said image data includes image data from at least two two-dimensional images of the subject's bone taken from at least two different angles;
    (b) combining said at least two two-dimensional images into a volumetric image dataset;
    (c) extracting a three-dimensional model representing the structure of trabecular bone from the volumetric image dataset;
    (d) simulating bone remodeling using said three-dimensional model; and
    (e) predicting structural strength of the bone based at least in part on the simulation of bone remodeling.

2. The method of claim 1, wherein said at least two two-dimensional images of the subject's bone include x-ray images taken using at least two different x-ray beam rotation angles.

3. A method for monitoring the ability of an agent to affect bone quality, the method comprising the steps of:
    (a) obtaining bone quality measurements on a subject by analyzing bone structure or bone density using the method according to claim 1;
    (b) administering the agent to the subject;
    (c) obtaining bone quality measurements of the subject after administration of the agent, wherein the bone quality measurements are obtained by analyzing bone structure or bone density using the method according to claim 1;
    (d) comparing bone quality measurements from steps (a) and (c), wherein a difference in bone quality measurements between steps (a) and (c) is indicative of the ability of the agent to affect bone quality.

4. The method of claim 3, wherein the bone quality measurements are bone density or bone structure measurements.

5. A method for analyzing bone structure or bone density using a computer system, the method comprising the steps of:
    (a) obtaining image data from at least two two-dimensional images of at least a portion of a subject's bone including trabecular bone, the at least two two-dimensional images taken from at least two different angles;
    (b) extracting a projection structure of trabecular bone from image data of each two-dimensional image of said at least two two-dimensional images;
    (c) converting said projection structures into a three-dimensional probable model representing the volumetric structure of the trabecular bone;
    (d) simulating bone remodeling using said model; and
    (e) predicting structural strength of the bone based at least in part on the simulation of bone remodeling.

6. The method of claim 5, wherein said at least two two-dimensional images of the subject's bone include x-ray images taken using at least two different x-ray beam rotation angles.

7. The method of claim 5, further including performing a quantitative analysis of bone microarchitecture in each projection structure of trabecular bone before converting said projection structures into said three-dimensional probable model.

8. The method of claim 7, wherein said converting said projection structures includes using said quantitative analysis of bone microarchitecture.

9. A method for monitoring the ability of an agent to affect bone quality, the method comprising the steps of:
    (a) obtaining bone quality measurements on a subject by analyzing bone structure or bone density using the method according to claim 5;
    (b) administering the agent to the subject;
    (c) obtaining bone quality measurements of the subject after administration of the agent, wherein the bone quality measurements are obtained by analyzing bone structure or bone density using the method according to claim 5;
    (d) comparing bone quality measurements from steps (a) and (c), wherein a difference in bone quality measurements between steps (a) and (c) is indicative of the ability of the agent to affect bone quality.

10. The method of claim 9, wherein the bone quality measurements are bone density or bone structure measurements.

11. A method for estimating future fracture risk in a subject, the method comprising the steps of:
    (a) obtaining two-dimensional image data of at least a portion of a subject's bone including trabecular bone, wherein said image data includes image data from at least two two-dimensional images of the subject's bone taken from at least two different angles;
    (b) combining said at least two two-dimensional images into a volumetric image dataset;
    (c) extracting a three-dimensional model representing the volumetric structure of trabecular bone from said volumetric image dataset;
    (d) simulating bone remodeling using said model;

(e) predicting structural strength of the bone based at least in part on the simulation of bone remodeling; and (f) comparing the predicted structural strength of the bone from the simulation of bone remodeling to measurements of population data, thereby predicting fracture risk in the subject.

12. The method of claim 11, wherein the simulation of bone remodeling is of therapeutic interventions.

13. The method of claim 11, wherein the simulation of bone remodeling is of disease progression.

14. The method of claim 11, wherein one or more steps are automated.

15. A method for estimating future fracture risk in a subject, the method comprising the steps of:

(a) obtaining at least two two-dimensional images of at least a portion of a subject's bone including trabecular bone, the at least two two-dimensional images taken from at least two different angles;

(b) extracting a projection structure of the trabecular bone from each two-dimensional image of said at least two two-dimensional images;

(c) converting said projection structures into a three-dimensional probable model representing the volumetric structure of trabecular bone;

(d) simulating bone remodeling using said probable model;

(e) predicting structural strength of the bone based at least in part on the simulation of bone remodeling; and (f) comparing the predicted structural strength of the bone from the simulation of bone remodeling to measurements of population data, thereby predicting fracture risk in the subject.

16. The method of claim 15, wherein the simulation of bone remodeling is of therapeutic interventions.

17. The method of claim 15, wherein the simulation of bone remodeling is of disease progression.

18. The method of claim 15, wherein one or more steps are automated.

\* \* \* \* \*